United States Patent [19]

Tokunaga et al.

[11] Patent Number: 4,866,064

[45] Date of Patent: Sep. 12, 1989

[54] 5H-1,3,4-THIADIAZOLO(3,2-A)PYRIMIDIN-5-ONE DERIVATIVES AND FUNGICIDAL COMPOSITIONS CONTAINING THE SAME

[75] Inventors: Yukio Tokunaga, Shizuoka; Yoshiyuki Kojima, Kakegawa; Shinichiro Maeno; Nobumitsu Sawai, both of Shizuoka; Yasuo Saso, Miyagi, all of Japan

[73] Assignees: Kumiai Chemical Industry Co., Ltd.; Ihara Chemical Industry Co., Ltd., both of Tokyo, Japan

[21] Appl. No.: 95,672

[22] Filed: Sep. 14, 1987

Related U.S. Application Data

[63] Continuation-in-part of Ser. No. 27,250, Mar. 18, 1987.

[30] Foreign Application Priority Data

Mar. 19, 1986 [JP] Japan .................... 61-061747

[51] Int. Cl.$^4$ ............ A01N 43/54; C07D 417/02
[52] U.S. Cl. .................... 514/258; 544/255
[58] Field of Search ............ 544/255; 514/258; 71/90

[56] References Cited

U.S. PATENT DOCUMENTS 4,742,063 5/1988 Tokunage ............ 514/258

FOREIGN PATENT DOCUMENTS 52-118494 10/1977 Japan .................... 544/255

OTHER PUBLICATIONS

Okabe (1975) J. Fac. Agr., Kyushu Univ., 19, pp. 91-102.
Suiko I (1977) Agr. Biol. Chem., 41(10), pp. 2047-2053.
Suiko II (1979) Agr. Biol. Chem., 43(4), pp. 747-752.

*Primary Examiner*—Donald G. Daus
*Attorney, Agent, or Firm*—Oblon, Spivak, McClelland, Maier & Neustadt

[57] ABSTRACT

A class of novel 5H-1,3,4-thiadizaolo[3,2-a]pyrimidin-5-one derivatives are disclosed. These compounds exhibit remarkable fungicidal activities for pathogenic fungi of cucumber gray mold, cucumber downy mildew, Alternaria sooty spot of Chinese mustard, apple Alternaria leaf spot, pear black spot, rice blast, tomato late blight, etc.

10 Claims, No Drawings

5H-1,3,4-THIADIAZOLO(3,2-A)PYRIMIDIN-5-ONE DERIVATIVES AND FUNGICIDAL COMPOSITIONS CONTAINING THE SAME

CROSS REFERENCE TO THE RELATED APPLICATION

This application is a continuation-in-part application of U.S. Ser. No. 027,250 filed Mar. 19, 1987.

FIELD OF THE INVENTION

This invention relates to a novel agricultural-horticultural fungicide. More particularly, this invention relates to a class of novel 5H-1,3,4-thiadiazolo[3,2-a]pyrimidin-5-one derivatives and fungicidal compositions containing the same.

BACKGROUND OF THE INVENTION

In the specification of Japanese Laying-Open patent publication No. 52-118494 (1977), it is described that a thiadiazolo[3,2-a]pyrimidinone derivative represented by the general formula

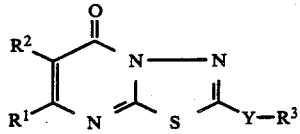

wherein $R^1$ stands for an alkyl group or an aryl group; $R^2$ stands for a hydrogen atom, a halogen atom, a nitro group, a carboalkoxy group or an alkyl group; $R^3$ stands for an alkyl group or an aralkyl group; and Y stands for —SO— or —SO$_2$—, exhibits an activity inhibiting proliferation of cancer cells and is useful as an anticancer agent.

In the specification of Japanese Laying-Open patent publication No. 58-177997 (1983), it is described that a thiadiazolopyrimidinone derivative represented by the general formula

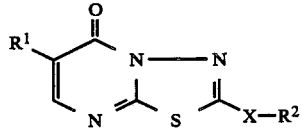

wherein $R^1$ stands for a 1 or 2H-tetrazol-5-yl group, a carboxy group or a lower alkoxycarbonyl group; $R^2$ stands for an aryl group or a heteroaryl group which may be substituted with an alkyl group, an alkoxy group, a hydroxy group or a halogen atom; X stands for an alkylene group, an alkenylene group, an alkynylene group or any of the above groups, to an end of which an oxygen atom, a sulfur atom or SO$_2$ is attached; wherein each of the groups represented by X may be substituted with one or more linear or cyclic alkyl groups or with the substituent $R^2$, and a physiologically acceptable salt thereof have excellent antiallergic activity.

As described above, there were known several thiadiazolopyrimidinone derivatives, which have a chemical structure similar to that of the compounds of the present invention. However, these are medicinals, and they do not clearly exhibit activities as pesticides.

We paid attention to the 5H-1,3,4-thiadiazolo[3,2-a]pyrimidin structure, which is the skeleton of many substances used as medicines, and we synthesized a number of derivatives thereof and studied their biological activities. As a result, we found that some specific compounds having the 5H-1,3,4-thiadiazolo[3,2-a]pyrimidin structure exhibit an excellent property as an agricultural-horticultural pesticide, and completed this invention.

That is to say, the object of this invention is to provide novel 5H-1,3,4-thiadiazolo[3,2-a]pyrimidin-5-one derivatives, useful agricultural-horticultural fungicidal compositions containing said derivatives, a process for preparing said derivatives as well as a class of novel compounds, which are the starting materials for preparation of said derivatives.

DISCLOSURE OF THE INVENTION

This invention provides a 5H-1,3,4-thiadiazolo[3,2-a]pyrimidin-5-one derivative represented by the general formula (I)

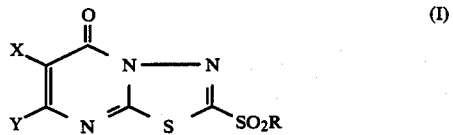

wherein
X stands for a hydrogen atom, a halogen atom, a linear or branched lower alkyl group, a lower alkoxy group, a lower acyl group, a trihalo-lower-alkoxy group, a lower alkynyl group, a phenyl group, a cyano group, a phenoxy group or a nitro group;
Y stands for a hydrogen atom, a halogen atom, a linear or branched lower alkyl group, a halo-lower-alkyl group, a lower alkoxy group, a lower alkynyl group, a phenyl-lower-alkynyl group, a lower-alkyl-amino group, or a cyano group; and
R stands for a linear or branched alkyl group, a cyclohexyl-lower-alkyl group, a lower alkenyl group, a cyclohexyl group, a phenoxy-lower-alkyl group, a halo-alkyl group, a halo-alkenyl group, a lower-alkoxycarbonyl-lower-alkyl group, a tri-lower-alkyl-silyl-lower-alkyl group, a phenyl-lower-alkyl group, an alkoxy-lower-alkyl group, a phenyl group which may be substituted with one or more halogen atoms, lower alkyl groups or nitro groups or lower alkoxy groups; a group represented by the general formula

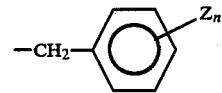

wherein
Z stands for a halogen atom, a lower alkyl group, a lower alkoxy group, a trihalo-lower-alkyl group or a nitro group, and n is an integer of 1 or 2, wherein the two substituents may be the same or different; with a proviso that when X is a hydrogen atom, a halogen atom, a nitro group, or an alkyl group and that Y is an alkyl group, R is not an alkyl group nor a phenyl-lower-alkyl group.

Further this invention provides a process for preparing a 5H-1,3,4-thiadiazolo[3,2-a]pyrimidin-5-one derivative represented by the general formula (I)

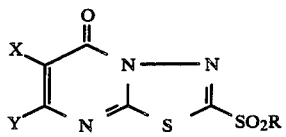

wherein
- X stands for a hydrogen atom, a halogen atom, a linear or branched lower alkyl group, a lower alkoxy group, a lower acyl group, a trihalo-lower-alkoxy group, a lower alkynyl group, a phenyl group, a cyano group, a phenoxy group or a nitro group;
- Y stands for a hydrogen atom, a halogen atom, a linear or branched lower alkyl group, a halo-lower-alkyl group, a lower alkoxy group, a lower alkynyl group, a phenyl-lower-alkynyl group, a lower-alkyl-amino group, or a cyano group; and
- R stands for a linear or branched alkyl group, a cyclohexyl-lower-alkyl group, a lower alkenyl group, a cyclohexyl group, a phenoxy-lower-alkyl group, a halo-alkyl group, a halo-alkenyl group, a lower-alkoxycarbonyl-lower-alkyl group, a tri-lower-alkyl-silyl-lower-alkyl group, a phenyl-lower-alkyl group, an alkoxy-lower-alkyl group, a phenyl group which may be substituted with one or more halogen atoms, lower alkyl groups or nitro groups or lower alkoxy groups; a group represented by the general formula

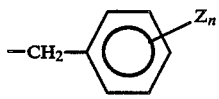

wherein
Z stands for a halogen atom, a lower alkyl group, a lower alkoxy group, a trihalo-lower-alkyl group or a nitro group, and n is an integer of 1 or 2, wherein the two substituents may be the same or different;
with a proviso that when X is a hydrogen atom, a halogen atom, a nitro group, or an alkyl group and that Y is an alkyl group, R is not an alkyl group nor a phenyl-lower-alkyl group,
comprising oxidizing a compound represented by the general formula (II)

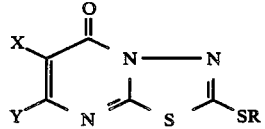

wherein X, Y and R are as defined above by a procedure known per se.

Still further, this invention provides a 5H-1,3,4-thiadiazolo[3,2-a]pyrimidin-5-one derivative represented by the general formula (II)

(II)

wherein
- X stands for a hydrogen atom, a halogen atom, a linear or branched lower alkyl group, a lower alkoxy group, a lower acyl group, a trihalo-lower-alkoxy group, a lower alkynyl group, a phenyl group, a cyano group, a phenoxy group or a nitro group;
- Y stands for a hydrogen atom, a halogen atom, a linear or branched lower alkyl group, a halo-lower-alkyl group, a lower alkoxy group, a lower alkynyl group, a phenyl-lower-alkynyl group, a lower-alkyl-amino group, or a cyano group; and
- R stands for a linear or branched alkyl group, a cyclohexyl-lower-alkyl group, a lower alkenyl group, a cyclohexyl group, a phenoxy-lower-alkyl group, a halo-alkyl group, a halo-alkenyl group, a lower-alkoxycarbonyl-lower-alkyl group, a tri-lower-alkyl-silyl-lower-alkyl group, a phenyl-lower-alkyl group, an alkoxy-lower-alkyl group, a phenyl group which may be substituted with one or more halogen atoms, lower alkyl groups or nitro groups or lower alkoxy groups; a group represented by the general formula —CH₂—⟨phenyl⟩—Zₙ wherein
Z stands for a halogen atom, a lower alkyl group, a lower alkoxy group, a trihalo-lower-alkyl group or a nitro group, and n is an integer of 1 or 2, wherein the two substituents may be the same or different;
with a proviso that when X is a hydrogen atom, a halogen atom, a nitro group, or an alkyl group and that Y is an alkyl group, R is not an alkyl group nor a phenyl-lower-alkyl group.

Still further, this invention provides an agricultural-horticultural fungicide composition comprising a 5H-1,3,4-thiadiazolo[3,2-a]pyrimidin-5-one derivative represented by the general formula (I)

(I)

wherein
- X stands for a hydrogen atom, a halogen atom, a linear or branched lower alkyl group, a lower alkoxy group, a lower acyl group, a trihalo-lower-alkoxy group, a lower alkynyl group, a phenyl group, a cyano group, a phenoxy group or a nitro group;
- Y stands for a hydrogen atom, a halogen atom, a linear or branched lower alkyl group, a halo-lower-alkyl group, a lower alkoxy group, a lower alkynyl group, a phenyl-lower-alkynyl group, a lower-alkyl-amino group, or a cyano group; and R stands for a linear or branched alkyl group, a cyclohexyl-lower-alkyl group, a lower alkenyl group, a cyclohexyl group, a phenoxy-lower-alkyl group, a halo-alkyl group, a halo-alkenyl group, a lower-alkoxycarbonyl-lower-alkyl group, a tri-lower-alkyl-silyl-lower-alkyl group, a phenyl-lower-alkyl group, an alkoxy-lower-alkyl group, a phenyl group which may be substituted with one or more halogen atoms, lower alkyl groups or nitro groups or lower alkoxy groups; a group represented by the general formula

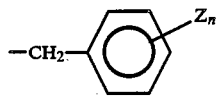

wherein

Z stands for a halogen atom, a lower alkyl group, a lower alkoxy group, a trihalo-lower-alkyl group or a nitro group, and n is an integer of 1 or 2, wherein the two substituents may be the same or different; with a proviso that when X is a hydrogen atom, a halogen atom, a nitro group, or an alkyl group and that Y is an alkyl group, P is not an alkyl group nor a phenyl-lower-alkyl group, and an agricultural-horticulturally acceptable carrier.

Of the compounds of the general formula (I), preferred are those of which X stands for a hydrogen atom, a halogen atom, a $C_{1-4}$-alkyl group, a $C_{1-3}$-alkoxy group, an ethynyl group, an acetyl group, a trifluoroethoxy group, a phenyl group, a phenoxy group, a nitro group or a cyano group; Y stands for a hydrogen atom, a halogen atom, a $C_{1-3}$-alkyl group, a $C_{1-2}$-alkoxy group, a $C_{2-3}$-alkynyl group, a chloromethyl group, a phenylethynyl group, a $C_{2-3}$-alkylamino group or a cyano group; and R stands for a $C_{1-9}$-alkyl group, a cyclohexylmethyl group, an allyl group, a cyclohexyl group, a phenoxyalkyl group, a haloalkyl group, a dichloroalkenyl group, an ethoxycarbonylbutyl group, an alkoxyalkyl group, a phenyl-$C_{1-4}$-alkyl group, a trimethylsilylpropyl group, a phenyl group which may be substituted with a halogen atom, a $C_{1-4}$-alkyl group, a $C_{1-3}$-alkoxy group, a nitro group; a group represented by the general formula

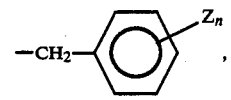

wherein Z stands for a halogen atom, a $C_{1-4}$-alkyl group, a $C_{1-3}$-alkoxy group, a trifluoromethyl group or a nitro group.

Examples of the compounds of the present invention represented by the general formula (I) are listed in Table 1. Each compound is hereinafter referred to by the compound number given in the table.

TABLE 1

![structure with X, Y on pyrimidine ring fused to N-N-C(SO2R)=C-S]

| Compound No. | X | Y | R | m.p. (°C.) refractive index ($n^{D20}$) |
|---|---|---|---|---|
| 1 | H | CH₃ | CH₂–C₆H₄–CH₃ | 157~162 |
| 2 | " | " | CH₂–C₆H₄–Cl | 192~194 |
| 3 | " | " | CH₂–C₆H₄–F | 212~216 |
| 4 | " | " | CH₂–C₆H₄–NO₂ | 210~213 |
| 5 | " | " | CH₂–C₆H₄–C₄H₉–t | 209~211 |

TABLE 1-continued $$\text{structure with X, Y, N-N, C=O, N=C-S-C=N, SO}_2\text{R}$$

| Compound No. | X | Y | R | m.p. (°C.) refractive index ($n^{D20}$) |
|---|---|---|---|---|
| 6 | " | " | $CH_2$–C$_6$H$_4$–CH$_3$ (o) | 164~168 |
| 7 | " | " | $CH_2$–C$_6$H$_4$–Cl (o) | 179~182 |
| 8 | " | " | $CH_2$–C$_6$H$_4$–CH$_3$ (m) | 156~160 |
| 9 | " | " | $CH_2$–C$_6$H$_4$–Cl (m) | 175.5~179 |
| 10 | " | " | $CH_2$–C$_6$H$_4$–OCH$_3$ (m) | 114~116 |
| 11 | " | " | $CH_2$–C$_6$H$_4$–CF$_3$ (m) | 95~98 |
| 12 | H | CH$_3$ | $CH_2$–C$_6$H$_3$(CH$_3$)$_2$ (2,4) | 150~152 |
| 13 | " | " | $CH_2$–C$_6$H$_3$(CH$_3$)$_2$ (2,5) | 185~187 |
| 14 | " | " | $CH_2$–C$_6$H$_3$Cl$_2$ (2,4) | 104~106 |
| 15 | " | " | $CH_2$–C$_6$H$_3$Cl$_2$ (3,4) | 208~210 |

TABLE 1-continued
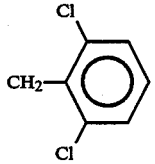
| Compound No. | X | Y | R | m.p. (°C.) refractive index ($n^{D20}$) |
|---|---|---|---|---|
| 16 | " | " | 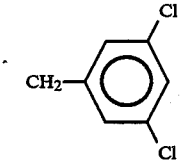 | 231~234 |
| 17 | " | " | 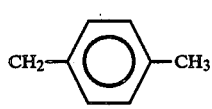 | 149~152 |
| 18 | $CH_3$ | H | 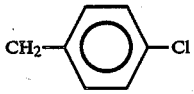 | 190~193 |
| 19 | " | " | 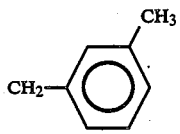 | 209~210 |
| 20 | " | " | 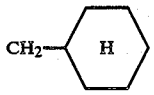 | 162~164 |
| 21 | H | " | $n\text{-}C_6H_{13}$ | 65~67 |
| 22 | " | " | $n\text{-}C_7H_{15}$ | 88~90 |
| 23 | $CH_3$ | " | $n\text{-}C_5H_{11}$ | 107~109 |
| 24 | " | " | $n\text{-}C_6H_{13}$ | 79~81 |
| 25 | " | " | $n\text{-}C_7H_{15}$ | 90~92 |
| 26 | $CH_3$ | H | $n\text{-}C_8H_{17}$ | 96~98 |
| 27 | " | " | 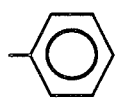 | 124~128 |
| 28 | $C_2H_5$ | " | $n\text{-}C_7H_{15}$ | 78~80 |
| 29 | $i\text{-}C_3H_7$ | " | $n\text{-}C_7H_{15}$ | 59~62 |
| 30 | H | Cl | $n\text{-}C_7H_{15}$ | 104~110 |
| 31 | " | F | $n\text{-}C_7H_{15}$ | 115~117 |
| 32 | $CH_3$ | Cl | $n\text{-}C_7H_{15}$ | 136~138 |
| 33 | " | F | $n\text{-}C_7H_{15}$ | 143~146 |
| 34 | H | $CH_3$ | 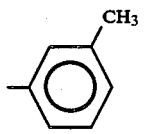 | 191~194 |
| 35 | " | " |  | 140~143 |

TABLE 1-continued
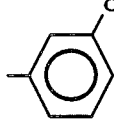
| Compound No. | X | Y | R | m.p. (°C.) refractive index ($n^{D20}$) |
|---|---|---|---|---|
| 36 | " | " | 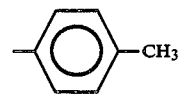 3-Cl-C6H4 | 209~215 |
| 37 | " | " | 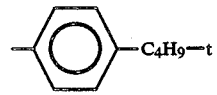 4-CH3-C6H4 | 207~208 |
| 38 | " | " | 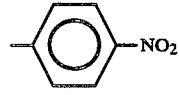 4-t-C4H9-C6H4 | 186~188 |
| 39 | " | " |  4-NO2-C6H4 | 214~216 |
| 40 | CH3 | H | 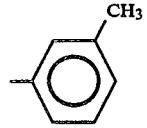 C6H5 | 198~200 |
| 41 | " | " | 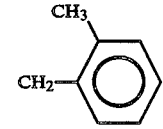 3-CH3-C6H4 | 156~158 |
| 42 | H | " | 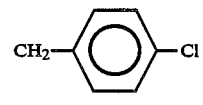 2-CH3-C6H4-CH2 | 135~138 |
| 43 | " | " | 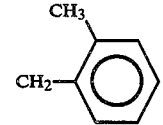 4-Cl-C6H4-CH2 | 179~188 |
| 44 | CH3 | " | 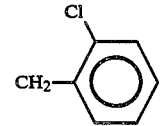 2-CH3-C6H4-CH2 | 183~186 |
| 45 | " | " | 2-Cl-C6H4-CH2 | 191~193 |
| 46 | " | " | 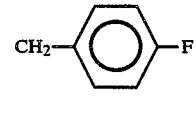 4-F-C6H4-CH2 | 200~203 |

TABLE 1-continued

[Structure: X, Y substituted triazine-thiadiazole with SO₂R group]

| Compound No. | X | Y | R | m.p. (°C.) refractive index ($n^{D20}$) |
|---|---|---|---|---|
| 47 | " | " | -CH₂-C₆H₃(CH₃)₂ (3,5-dimethylbenzyl) | 199~204 |
| 48 | " | " | -C₆H₄-CH₃ (p-tolyl) | 183~185 |
| 49 | " | " | -C₆H₄-Cl (p-chlorophenyl) | 205~208 |
| 50 | " | " | -C₆H₄-F (p-fluorophenyl) | 178~180 |
| 51 | " | " | n-C₃H₇ | 149~151 |
| 52 | " | " | n-C₄H₉ | 107.5~109 |
| 53 | C₂H₅ | " | -CH₂-C₆H₄-CH₃ | 67~77 |
| 54 | C₂H₅ | H | n-C₆H₁₃ | 67~69 |
| 55 | i-C₃H₇ | " | -CH₂-C₆H₄-Cl (o-chlorobenzyl) | 162~163.5 |
| 56 | " | " | -CH₂-C₆H₄-CH₃ | 141~146 |
| 57 | " | " | -C₆H₅ (phenyl) | 135~138 |
| 58 | " | " | n-C₄H₉ | 105~106 |
| 59 | " | " | n-C₅H₁₁ | 108~109 |
| 60 | " | " | n-C₆H₁₃ | 75~76 |
| 61 | i-C₄H₉ | " | -CH₂-C₆H₄-CH₃ | 115~121 |
| 62 | " | " | -CH₂-C₆H₄-C₂H₅ | 134~138 |

TABLE 1-continued

| Compound No. | X | Y | R | m.p. (°C.) refractive index ($n^{D20}$) |
|---|---|---|---|---|
| 63 | " | " | CH$_2$–C$_6$H$_4$–Cl (p) | 155~158 |
| 64 | " | " | n-C$_4$H$_9$ | 84~87 |
| 65 | H | " | CH$_2$–(2,5-dimethylphenyl) | 206~208 |
| 66 | " | n-C$_3$H$_7$ | CH$_2$–C$_6$H$_4$–CH$_3$ (p) | 163~165 |
| 67 | " | " | CH$_2$–C$_6$H$_4$–Cl (p) | 216~218 |
| 68 | H | n-C$_3$H$_7$ | C$_6$H$_5$ | 139~141 |
| 69 | " | Cl | n-C$_4$H$_9$ | 140~142 |
| 70 | " | " | n-C$_6$H$_{13}$ | 118~121 |
| 71 | " | F | n-C$_5$H$_{11}$ | 127~130 |
| 72 | " | " | n-C$_6$H$_{13}$ | 107~108 |
| 73 | CH$_3$ | CH$_3$ | C$_6$H$_5$ | 195~197 |
| 74 | " | Cl | C$_6$H$_5$ | 258~261 |
| 75 | " | " | n-C$_3$H$_7$ | 196~197 |
| 76 | " | " | n-C$_4$H$_9$ | 151~153 |
| 77 | " | " | n-C$_5$H$_{11}$ | 156~157 |
| 78 | " | " | n-C$_6$H$_{13}$ | 135~139 |
| 79 | " | F | n-C$_4$H$_9$ | 131~132 |
| 80 | " | " | n-C$_5$H$_{11}$ | 128~132 |
| 81 | " | " | n-C$_6$H$_{13}$ | 143~145 |
| 82 | C$_6$H$_5$ | H | CH$_2$–C$_6$H$_4$–CH$_3$ (p) | 186~190 |
| 83 | " | " | C$_6$H$_5$ | 201~203 |

TABLE 1-continued

[Structure: X-C(=Y)-C(=O)-N linked to triazole-thiadiazole ring with SO₂R]

| Compound No. | X | Y | R | m.p. (°C.) refractive index ($n^{D20}$) |
|---|---|---|---|---|
| 84 | " | " | n-C$_4$H$_9$ | 96~100 |
| 85 | " | " | n-C$_6$H$_{13}$ | 94~95 |
| 86 | C≡CH | " | " | 165~175 |
| 87 | " | " | n-C$_7$H$_{15}$ | 180~182 |
| 88 | OCH$_3$ | " | CH$_2$-C$_6$H$_4$-CH$_3$ | 170~172 |
| 89 | " | " | CH$_2$-C$_6$H$_4$-C$_2$H$_5$ | 112~115 |
| 90 | " | " | CH$_2$-C$_6$H$_4$-C$_3$H$_7$-i | 151~153 |
| 91 | " | " | CH$_2$-C$_6$H$_4$-Cl | 194~196 |
| 92 | " | " | C$_6$H$_5$ | 166~175 |
| 93 | " | " | n-C$_6$H$_{13}$ | 110~111 |
| 94 | " | " | n-C$_7$H$_{15}$ | 106~109 |
| 95 | " | " | n-C$_9$H$_{19}$ | 104~105.5 |
| 96 | OC$_2$H$_5$ | H | CH$_2$-C$_6$H$_4$-CH$_3$ | 184~187 |
| 97 | " | " | n-C$_6$H$_{15}$ | 72~75 |
| 98 | OC$_6$H$_5$ | " | CH$_2$-C$_6$H$_4$-CH$_3$ | 148~153 |
| 99 | " | " | C$_6$H$_5$ | 201~205 |
| 100 | " | " | n-C$_4$H$_9$ | 133~135 |
| 101 | " | " | n-C$_6$H$_{13}$ | 97~99 |
| 102 | Cl | " | CH$_2$-C$_6$H$_4$-CH$_3$ | 209~213 |
| 103 | " | " | n-C$_5$H$_{11}$ | 140~142 |
| 104 | " | " | n-C$_6$H$_{13}$ | 142~143 |
| 105 | " | " | n-C$_7$H$_{15}$ | 145~147 |
| 106 | " | " | n-C$_8$H$_{17}$ | 146~148 |

TABLE 1-continued

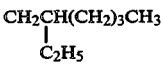

| Compound No. | X | Y | R | m.p. (°C.) refractive index ($n^{D20}$) |
|---|---|---|---|---|
| 107 | " | " | CH$_2$CH(CH$_2$)$_3$CH$_3$ \| C$_2$H$_5$ | $n_D^{20}$ 1.5785 |
| 108 | F | " |  CH$_2$—⟨ ⟩—CH$_3$ | 225~228 |
| 109 | " | " |  CH$_2$—⟨ ⟩—C$_2$H$_5$ | 190~191 |
| 110 | F | H | n-C$_6$H$_{13}$ | 75~76 |
| 111 | Br | " | n-C$_7$H$_{15}$ | 136~140 |
| 112 | NO$_2$ | NHC$_3$H$_7$—i | n-C$_7$H$_{15}$ | 124~125 |
| 113 | H | C≡CH | n-C$_6$H$_{13}$ | 152~155 |
| 114 | " | " | n-C$_7$H$_{15}$ | 146~149 |
| 115 | " | C≡CCH$_3$ | n-C$_6$H$_{13}$ | 122~125 |
| 116 | " | " | n-C$_7$H$_{15}$ | 127~129 |
| 117 | " | CH$_2$Cl | 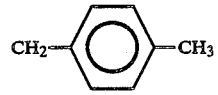 CH$_2$—⟨ ⟩—CH$_3$ | 194~198 |
| 118 | " | " | n-C$_7$H$_{15}$ | 95~97 |
| 119 | Cl | Cl | n-C$_5$H$_{11}$ | 207~209 |
| 120 | " | " | n-C$_6$H$_{13}$ | 194~198 |
| 121 | " | F | " | 185~188 |
| 122 | CH$_3$ | H |  ⟨ ⟩—OCH$_3$ | 186~188 |
| 123 | H | CH$_3$ | 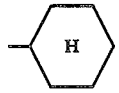 ⟨ ⟩—H | 146~150 |
| 124 | H | CH$_3$ | CH$_2$CH=CH$_2$ | 133~135 |
| 125 | " | " | 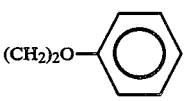 (CH$_2$)$_2$O—⟨ ⟩ | 156~158 |
| 126 | " | " | (CH$_2$)$_4$CO$_2$C$_2$H$_5$ | 138~140 |
| 127 | " | " | (CH$_2$)$_6$Cl | 126~128 |
| 128 | " | " | (CH$_2$)$_3$CH=CCl$_2$ | 106~108 |
| 129 | Cl | H |  CH$_2$—⟨ ⟩—C$_2$H$_5$ | 197~203 |
| 130 | H | " | 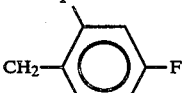 CH$_2$—⟨ ⟩ with F at 2,4 positions | 191~194 |

TABLE 1-continued
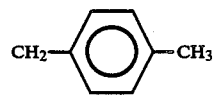
| Compound No. | X | Y | R | m.p. (°C.) refractive index ($n^{D20}$) |
|---|---|---|---|---|
| 131 | OCH$_2$CF$_3$ | " | 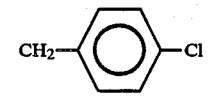 | 160~164 |
| 132 | F | " | 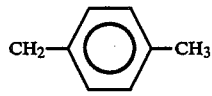 | 191~194 |
| 133 | H | " | 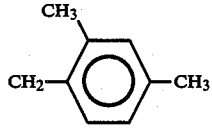 | 175~176 |
| 134 | " | " | 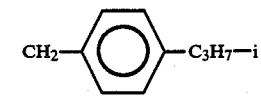 | 113~117 |
| 135 | " | " |  | 175~177 |
| 136 | OC$_3$H$_7$—n | " | 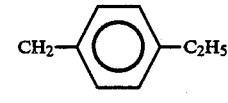 | 144~147 |
| 137 | H | " |  | 163~165 |
| 138 | H | H | 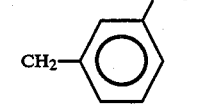 | 210~213 |
| 139 | " | " | 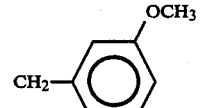 | 160~161.5 |
| 140 | " | " | 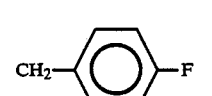 | 142~145 |
| 141 | Cl | " |  | 233~235 |

TABLE 1-continued structure: X,Y-substituted with C(=O)-N-N=, N-C(=S)-N, SO₂R

| Compound No. | X | Y | R | m.p. (°C.) refractive index ($n^{D20}$) |
|---|---|---|---|---|
| 142 | " | " | CH₂-(2,4-difluorophenyl) | 201~203 |
| 143 | " | " | CH₂-(2-chlorophenyl) | 193~197 |
| 144 | H | C₂H₅ | CH₂-(4-methylphenyl) | 159~163 |
| 145 | OC₂H₅ | H | CH₂-(4-chlorophenyl) | 182~185 |
| 146 | Cl | CH₃ | CH₂-(4-methylphenyl) | 217~221 |
| 147 | OCH₃ | H | CH₂-(2,6-dimethylphenyl) | 154~155 |
| 148 | " | " | CH₂-(2,4-dichlorophenyl) | 184~185 |
| 149 | " | " | CH₂-(2,4-difluorophenyl) | 179~180 |
| 150 | F | " | CH₂-(4-fluorophenyl) | 231~233 |
| 151 | H | " | CH₂-(2,6-dimethylphenyl) | 176~179 |
| 152 | F | CH₃ | CH₂-(4-chlorophenyl) | 218~219 |

TABLE 1-continued
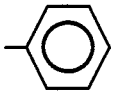
| Compound No. | X | Y | R | m.p. (°C.) refractive index ($n_D^{20}$) |
|---|---|---|---|---|
| 153 | H | $C_2H_5$ | 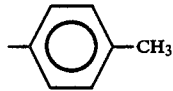 | 155~158 |
| 154 | $CH_3$ | $CH_3$ | 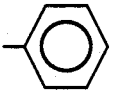 —$CH_3$ | 223~227 |
| 155 | F | H | 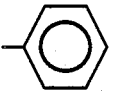 | 199~201 |
| 156 | Cl | $CH_3$ | 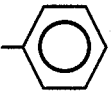 | 266~269 |
| 157 | " | H | 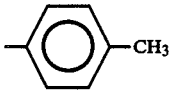 | 264~267 |
| 158 | F | " | 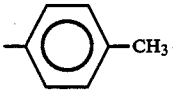—$CH_3$ | 215~218 |
| 159 | $OCH_3$ | " | 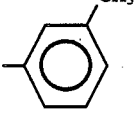—$CH_3$ | 167~169 |
| 160 | H | $C_2H_5$ | $CH_3$ 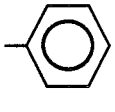 | 140~142 |
| 161 | F | $CH_3$ | 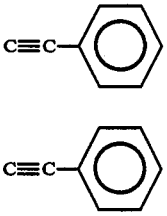 | 237.5~238.5 |
| 162 | Cl | H | n-$C_9H_{19}$ | 146~148 |
| 163 | $NO_2$ | Cl | n-$C_6H_{13}$ | 182~185 |
| 164 | H | CN | n-$C_6H_{13}$ | 144~146 |
| 165 | " | C≡C—⬡ | n-$C_6H_{13}$ | 134~137 |
| 166 | H | C≡C—⬡ | n-$C_7H_{15}$ | 127~129 |

TABLE 1-continued

| Compound No. | X | Y | R | m.p. (°C.) refractive index ($n^{D20}$) |
|---|---|---|---|---|
| 167 | " | CN | n-$C_7H_{15}$ | 114~119 |
| 168 | F | H | n-$C_7H_{15}$ | 92~93.5 |
| 169 | " | " | n-$C_8H_{17}$ | 71~77 |
| 170 | $NO_2$ | I | n-$C_6H_{13}$ | 159~161 |
| 171 | H | $CH_3$ | $(CH_2)_4O$-Ph | 150~152 |
| 172 | " | " | $(CH_2)_2OC_6H_{13}$ | 48~54 |
| 173 | " | " | $CH_2C(CH_3)_2$-Ph | 198~201 |
| 174 | CN | H | n-$C_6H_{13}$ | 146~150 |
| 175 | $NO_2$ | $OC_2H_5$ | n-$C_6H_{13}$ | 134~136 |
| 176 | " | $OCH_3$ | n-$C_6H_{13}$ | 150~152 |
| 177 | Cl | C≡CH | n-$C_6H_{13}$ | 150~153 |
| 178 | " | CN | n-$C_6H_{13}$ | 171~174 |
| 179 | $NO_2$ | $NHC_2H_5$ | n-$C_6H_{13}$ | 144~146 |
| 180 | $COCH_3$ | H | n-$C_6H_{13}$ | 124~125 |
| 181 | H | $CH_2Cl$ | n-$C_6H_{13}$ | 69~70 |
| 182 | Cl | " | n-$C_6H_{13}$ | 122~124 |
| 183 | $OCH_3$ | H | n-$C_8H_{17}$ | 109~110 |
| 184 | Cl | " | $CH_3$ | 225~228 |
| 185 | " | " | $CH_2CF_3$ | 187~190 |
| 186 | " | " | $CH_2CH_2$-Ph | 178~181 |
| 187 | " | " | $CH_2CH(C_2H_5)_2$ | 106~107.5 |
| 188 | $NO_2$ | Cl | n-$C_7H_{15}$ | 173~176 |
| 189 | " | $OCH_3$ | n-$C_7H_{15}$ | 153~154.5 |
| 190 | $COCH_3$ | H | n-$C_7H_{15}$ | 131.5~133.5 |
| 191 | CN | " | n-$C_7H_{15}$ | 130~132 |
| 192 | " | " | n-$C_8H_{17}$ | 122~124 |
| 193 | " | $CH_3$ | n-$C_7H_{15}$ | 172~175 |
| 194 | $OCH_3$ | H | $CH_2CH(C_2H_5)C_4H_9$—n | $n_D^{20}$ 1.5612 |
| 195 | Cl | " | $(CH_2)_3C_3H_7$—i | 151~153 |
| 196 | " | " | $(CH_2)_2CH(CH_3)C_2H_5$ | 130~132 |
| 197 | " | " | $CH_2CH(CH_3)C_3H_7$—n | 125~127 |
| 198 | $OCH_3$ | " | $(CH_2)_3Si(CH_3)_3$ | 112~114 |
| 199 | H | $CH_3$ | $(CH_2)_3Si(CH_3)_3$ | 155~157 |
| 200 | CN | F | n-$C_7H_{15}$ | 165~167 |
| 201 | $CH_3$ | CN | n-$C_6H_{13}$ | 134~135 |
| 202 | CN | H | $CH_2CH(C_2H_5)C_4H_9$—n | 87.5~89 |
| 203 | $COCH_3$ | " | n-$C_8H_{17}$ | 132~134 |
| 204 | " | " | $CH_2CH(C_2H_5)C_4H_9$—n | 73~76 |
| 205 | Cl | " | $CH_2$-cyclohexyl | 188~190 |
| 206 | " | F | n-$C_5H_{11}$ | 188~191 |
| 207 | " | $CH_2Cl$ | n-$C_7H_{15}$ | 143~145 |
| 208 | $CH_3$ | H | $CH_2CH(C_2H_5)C_4H_9$—n | $n_D^{20}$ 1.5611 |
| 209 | Cl | " | cyclohexyl | 157~160 |

TABLE 1-continued

[Structure shown at top of table with substituents X, Y on left side and SO₂R on right side of the bicyclic system]

| Compound No. | X | Y | R | m.p. (°C.) refractive index ($n^{D20}$) |
|---|---|---|---|---|
| 210 | " | " | (CH₂)₃CH=C(Cl)(Cl) | 122–126 |
| 211 | H | CN | n-$C_8H_{17}$ | 111–112 |
| 212 | " | " | CH₂CH($C_2H_5$)$C_4H_9$—n | 105–107 |
| 213 | F | H | " | 94–99 |
| 214 | OCH₃ | " | CH₂-C₆H₄(Cl) | 173–175 |
| 215 | " | " | CH₂-C₆H₃(CH₃)₂ | 191.5–194 |
| 216 | " | " | CH₂-C₆H₃(Cl)(F) | 195–198 |

Of these compounds, preferred are compounds of the general formula (I) wherein X stands for a hydrogen atom, a chlorine atom, a fluorine atom, a $C_{1-4}$-alkyl group, a $C_{1-3}$-alkoxy group, an ethynyl group, an acetyl group, a nitro group or a cyano group; Y stands for a hydrogen atom, a chlorine atom, a fluorine atom, a $C_{1-3}$-alkyl group, a $C_{1-3}$-alkoxy group, a $C_{2-3}$-alkynyl group or a cyano group, and R stands for a $C_{1-9}$-alkyl group, a trimethylsilylpropyl group, a phenethyl group, a phenyl group which may be substituted with one or two chlorine or fluorine atoms or $C_{1-4}$-alkyl groups or a bnezyl group substituted with one or two chlorine or fluorine atoms or one or two $C_{1-4}$-alkyl groups.

More preferred are compounds of the general formula (I) wherein X stands for a hydrogen atom, a chlorine or fluorine atom, a methyl group, a methoxy group, an ethynyl group, a cyano group or an acetyl group; Y stands for a hydrogen atom, a chlorine or fluorine atom, an ethynyl group, a propynyl group or a cyano group; and R stands for a $C_{4-9}$-alkyl group, a trimethylsilylpropyl group, a phenyl group which may be substituted with a chlorine or fluorine atom or a methyl group or a benzyl group substituted with one or two chlorine or fluorine atoms or one or two methyl groups.

One group of most preferred compounds are compounds of the general formula (I) wherein X stands for a hydrogen atom, a chlorine or fluorine atom or a methyl group; Y stands for a hydrogen atom, an ethynyl group or a propynyl group; and R stands for a $C_{4-9}$-alkyl group or a methylbenzyl group.

Another group of most preferred compounds are compounds of the general formula (I) wherein X stands for a chlorine or fluorine atom, a methyl group, an ethynyl group or a cyano group; Y stands for a hydrogen atom or a chlorine or fluorine atom; and R stands for a $C_{4-9}$-alkyl.

Still another group of most preferred compounds are compounds of the general formula (I), wherein X stands for a chlorine or fluorine atom, a methoxy group or an acetyl group; Y stands for a hydrogen atom; and R stands for a $C_{4-9}$-alkyl group, a benzyl group substituted with one or two chlorine or fluorine atoms or one or two methyl group.

Still another group of most preferred compounds are compounds of the general formula (I), wherein X stands for a hydrogen atom or a chlorine or fluorine atom; Y stands for a cyano group, an ethynyl group or a propynyl group; and R stands for a $C_{4-9}$-alkyl group.

Still another group of most preferred compounds are compounds of the general formula (I), wherein X stands for a hydrogen atom, a chlorine atom, a fluorine atom, a methyl group or a methoxy group; Y stands for a hydrogen atom; and R stands for a benzyl group substituted with one or two chlorine or fluorine atoms or one or two methyl groups.

Still another group of most preferred compounds are compounds of the general formula (I), wherein X stands for a chlorine atom; Y stands for a hydrogen atom or a chlorine or fluorine atom, and R stands for a C$_{4-9}$-alkyl group. are compounds of the general formula (I), wherein X stands for a chlorine atom; Y stands for a hydrogen atom; and R stand for a C$_{5-6}$-alkyl group.

The most preferred compounds are:

6-Chloro-2-hexanesulfonyl-5H-1,3,4-thiadiazolo[3,2-a]pyrimidin-5-one

2-Hexanesulfonyl-7-(1-propynyl)-5H-1,3,4-thiadiazolo[3,2-a]pyrimidin-5-one

7-Ethynyl-2-hexanesulfonyl-5H-1,3,4-thiadiazolo[3,2-a]pyrimidin-5-one

6-Chloro-7-fluoro-2-hexanesulfonyl-5H-1,3,4-thiadiazolo[3,2-a]pyrimidin-5-one

7-Ethynyl-6-chloro-2-hexanesulfonyl-5H-1,3,4-thiadiazolo[3,2-a]pyrimidin-5-one

6-Methoxy-2-octanesulfonyl-5H-1,3,4-thiadiazolo[3,2-a]pyrimidin-5-one

6-Cyano-2-heptanesulfonyl-5H-1,3,4-thiadiazolo[3,2-a]pyrimidin-5-one

6-Acetyl-2-heptanesulfonyl-5H-1,3,4-thiadiazolo[3,2-a]pyrimidin-5-one

6-Chloro-7-fluoro-2-pentanesulfonyl-5H-1,3,4-thiadiazolo[3,2-a]pyrimidin-5-one

The compounds of the present invention can be prepared by oxidizing a compound represented by the general formula (II)

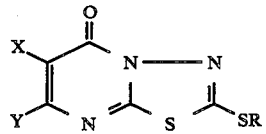

wherein X, Y and R are as defined with respect to the general formula (I).

The oxidation of the compounds of the general formula (II) can be performed by any method employed for oxidation of organic sulfide compounds.

Examples of the employable oxidizing agents are hydrogen peroxide, organic peracids such as m-chloroperbenzoic acid, "OXONE" (trade name, a reagent containing potassium hydrogen peroxosulfate marketed by Du Pont Company), etc.

In addition to the oxidation reagent, an acid catalyst such as acetic acid, a metallic catalyst such as sodium tungstate, for instance, can be used in order to promote the oxidation reaction.

Examples of the solvents used for the oxidation reaction are water; halogenated hydrocarbon such as dichloromethane, chloroform, carbon tetrachloride, chlorobenzene, etc.; fatty acids such as acetic acid, propionic acid, etc.; ketones such as acetone, methylethyl ketone, etc.; amides such as dimethylformamide, dimethylacetamide, etc.; alcohols such as methyl alcohol, ethyl alcohol, etc.; hydrocarbons such as hexane, petroleum ether, benzene, etc.

Oxidation is carried out in a temperature range of −20° C. to the boiling temperature of the used solvent. The amount of the used oxidizing agent is usually twice the equivalent quantity of the used compound of the general formula (II) or more, but there is no strict limitation therefor.

The compounds of the general formula (II) are novel substances and can be prepared from a compound of the general formula (III):

wherein R is as defined above, by the four methods described below depending upon the kind of substituents.

The compound of the general formula (III) can be prepared by a generally employed method for preparing known 1,3,4-thiadiazoles in accordance with the following reaction scheme:

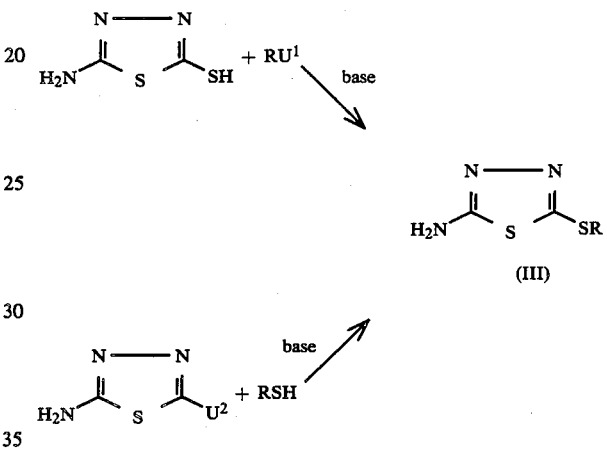

wherein R is as defined above and U$^1$ stands for a halogen atom, a benzenesulfonyloxy group, a substituted benzenesulfonyloxy group; and U$^2$ stands for a halogen atom.

The four methods for preparing compounds of the general formula (II) are as follows.

Process A

Compounds of the general formula (II) wherein R is as defined above, X is a hydrogen atom, a halogen atom or an alkyl group (designated as X$^1$); and Y is an alkyl group or a haloalkyl group (designated as Y$^1$) can be prepared by reacting a compound of general formula (III) with a β-keto ester derivative of the general formula (IV):

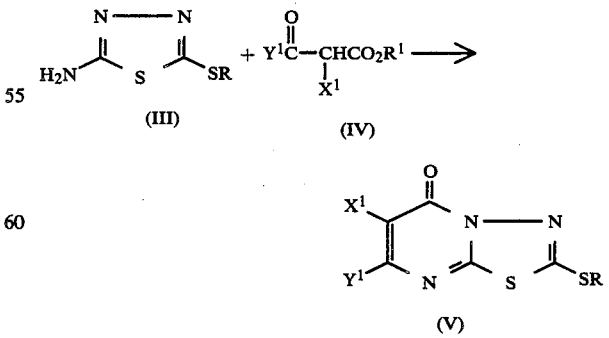

wherein R is as defined above, X$^1$ and Y$^1$ are as defined above under Process A, and R$^1$ stands for an alkyl group.

The reaction is carried out in a high-boiling solvent, or in the presence of a condensation reagent such as polyphosphoric acid, boron trifluoride etherate, sulfuric acid, etc. in the presence or absence of a relatively high-boiling solvent such as xylene.

Compounds of the general formula (IV) are known or otherwise can be prepared by a conventional process. Some of them are commercially available.

Of the compounds of the general formula (V), compounds, of which $X^1$ is a halogen atom, can be prepared by halogenating a corresponding compound of which $X^1$ is a hydrogen atom. As halogenating agents, chlorine, bromine, sulfuryl chloride, iodine monochloride, etc. can be used, for instance. If desired, a metal halide such as zinc chloride, ferric halide, etc. and pyridine, etc. can be used as a catalyst. Also, pyridine, zinc chloride, etc. can be used as a hydrogen halide remover.

A halogen atom as a substituent $X^1$ in the general formula (V), preferably an iodine, can be converted to a cyano group. As a preferred cyanizing agent, sodium cyanide and cuprous cyanide are simultaneously used in the presence of dimethylformamide solvent.

Process B

Compounds of the general formula (II), wherein X is a hydrogen atom, a halogen atom, a linear or branched alkyl group, a phenyl group, an alkoxy group, a phenoxy group or a trifluoroalkoxy group (designated as $X^2$); and Y is a hydrogen atom, can be prepared by reacting a compound of the general formula (III) with a β-formyl ester derivative or a 2-propenoate ester derivative (VI):

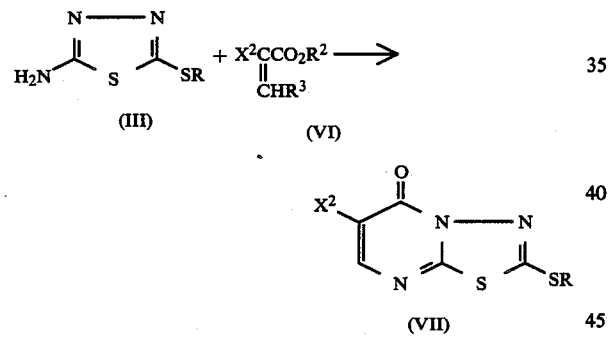

wherein R is as defined above, $X^2$ is as defined above under Process B, $R^2$ stands for an alkyl group, and $R^3$ stands for a hydroxy group or an alkoxy group. The reaction can be carried out in the same manner as in the above-described Process A.

Compounds of the general formula (VII) wherein $X^2$ is a halogen atom can be prepared by halogenating a compound of the general formula (VII) wherein $X^2$ is a hydrogen atom. Further, the halogen atom, preferably an iodine atom as a substituent $X^2$ can be converted to a cyano group or an alkynyl group. The halogenation and the cyanization can be effected as described above with respect to Process A.

Compounds of the general formula (VII) wherein $X^2$ is an alkynyl group can be prepared by reacting a compound of the general formula (VII) wherein $X^2$ is a halogen atom, preferably an iodine atom, with an alkyne compound such as an alkylacetylene, ethynyltrimethylsilane, etc. in the presence of a catalyst such as bis(triphenylphosphine)palladium (II) chloride, cuprous iodide, etc. and a hydrogen halide remover such as triethylamine. If necessary, the protecting group such as trimethylsilyl which is bonded to the alkynyl group is removed with a base such as potassium carbonate, tetralkylammonium fluoride, etc.

Compounds of the general formula (VI) are known or can be prepared by a generally employed method. Some of them are commercially available. Process C Compounds of the general formula (II), wherein R is as defined above, X is a hydrogen atom or an alkyl group (designated as $X^4$), Y is a halogen atom (designated as $Y^2$) or an alkynyl group or a cyano group (designated as $Y^3$) can be prepared by the following steps:

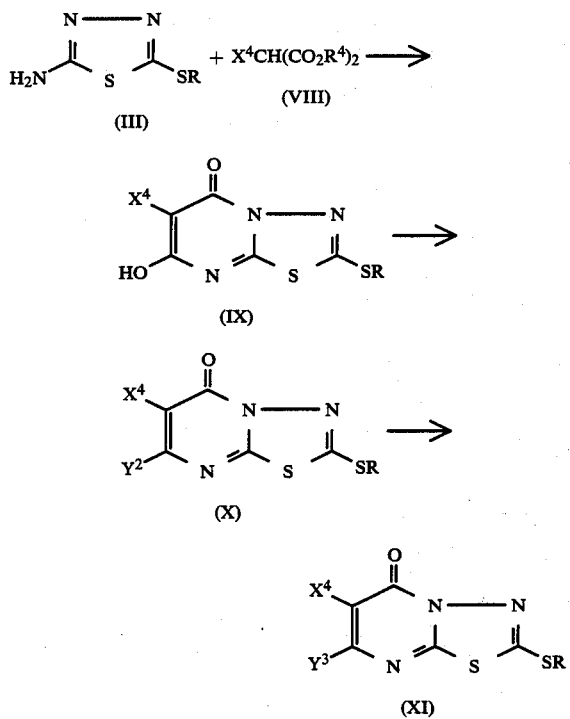

wherein R is as defined above, $X^4$, $Y^2$ and $Y^3$ are as defined above under Process C, and $R^4$ stands for a phenyl group or a substituted phenyl group.

The reaction of a compound of the general formula (III) and a compound of the general formula (VIII) is carried out in a relatively high-boiling solvent in accordance with the procedure described in Pharmacie 33, H11~13 (1978). A compound of the general formula (IX) can be converted to the corresponding compound of the general formula (X). If desired, the compound of the general formula (X) is subjected to halogen exchange. the halogen atom, preferably an iodine atom, can be converted to an alkynyl or a cyano group.

Examples of the usable halogenating agents are phosphorus oxychloride, phosphorus pentachloride, etc. If desired, a solvent such as toluene, a hydrogen halide remover such as N,N-dimethylaniline, etc. can be used. Halogen exchange can be performed using hydroiodic acid, potassium fluoride, etc.

Compounds of the general formula (XI) wherein $Y^3$ is an alkynyl group or a cyano group can be prepared by converting the halogen atom $Y^2$, preferably an iodine atom, of a compound of the general formula (X) to an alkynyl group or a cyano group in accordance with the alkynylation procedure described in Process B or the cyanization procedure described in Process A.

The hydrogen atom as a substituent $X^4$ of a compound of the general formula (IX), (X) or (XI) can be replaced with a halogen atom.

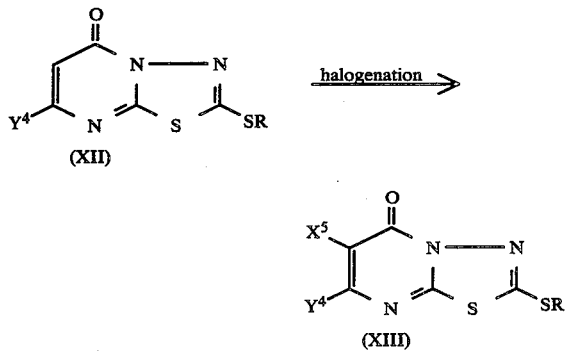

wherein R is as defined above, $X^5$ stands for a halogen atom and $Y^4$ stands for a hydroxy group, a halogen atom, an alkynyl group or cyano group. A halogen atom as the substituent $X^5$, preferably an iodine atom, can be converted to a cyano group.

The halogenation or cyanization can be performed by the same procedure as the halogenation or cyanization of the 6-position described in Process A. A compound of the general formula (XIII) wherein $Y^4$ is a hydroxy group can be halogenated by the same procedure as the halogenation of the 7-position of a compound of the general formula (IX).

Compounds of the general formula (IX) wherein $X^4$ is a hydrogen atom, can be nitrated, and thereafter the hydroxy group at the 7-position can be converted to a halogen atom, and further the halogen atom can be converted to an alkoxy group or an alkylamino group.

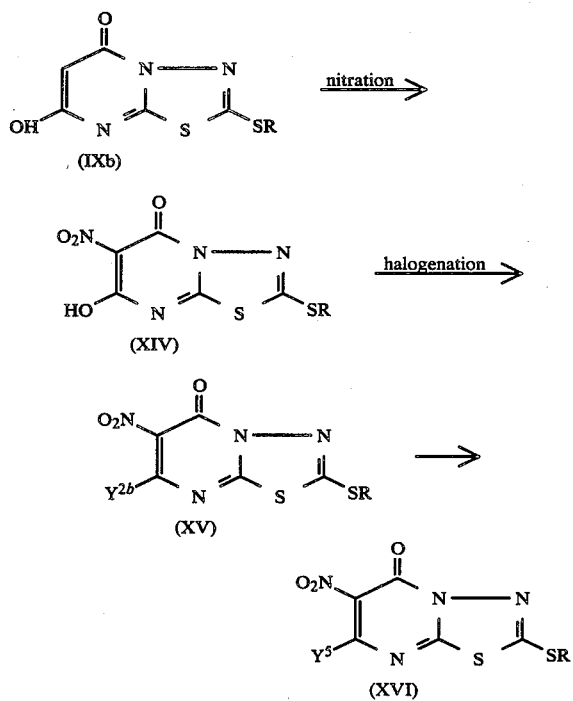

wherein R is as defined above. $Y^{2b}$ stands for a halogen atom, $Y^5$ stands for an alkoxy group or an alkylamino group.

Compounds of the general formula (XIV) can be prepared by treating a compound of the formula (IXb) with fuming nitric acid, in the presence of a solvent such as acetic acid if desired. Compounds of the formula (XV) can be prepared in the same manner as the preparation of compounds of the formula (X). Compounds of the formula (XVI) can be prepared by reacting a compound of the formula (XV) with an alcohol or an alkylamine in the presence of a hydrogen halide remover such as pyridine, and a solvent if desired.

Compounds of formula (VIII) are known or can be prepared by any conventional method. Process D Compounds of the formula (II) wherein X is an acetyl group can be prepared by the following process:

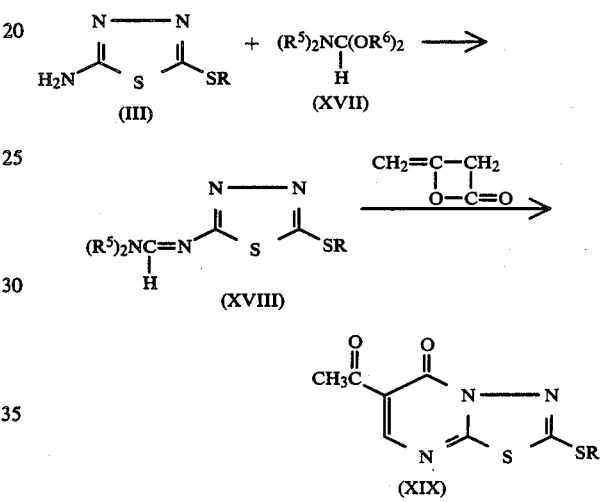

wherein R is as defined above with respect to the general formula (I), $R^5$ and $R^6$ stand for an alkyl group.

That is, a compound of the general formula (III) and a dialkylformamidodialkylacetal of the formula (XVII) are reacted to form a compound of the general formula (XVIII), and the latter is reacted with diketene to form a compound of the general formula (XIX).

The compounds of the present invention can be used as an agricultural-horticultural fungicide per se. However, they are usually prepared into a preparation in the form of dust, emulsifiable concentrate, granule or pellet by adding a carrier, surfactant, dispersant, or adjuvant by a conventional method.

Preferred carriers include solid carriers such as talc, bentonite, clay, kaolin, diatomaceous earth, white carbon, virmiculite, slaked lime, siliceous sand, ammonium sulfate, urea, etc. and liquid carriers such as isopropyl alcohol, xylene, cyclohexanone, etc.

Examples of the employable surfactants and dispersants are alcohol sulfate salts, alkylsulfonic acid salts, lignosulfonic acid salts, polyoxyethyleneglycol ether, polyoxyethylene alkylaryl ether, polyoxyethylene sorbitan monoalkylate, etc. As adjuvants, carboxymethyl cellulose, polyethylene glycol, gum arabic, etc. for instance can be used. The preparations are diluted to a suitable concentration and sprayed. Or otherwise, they are directly applied.

The concentration of the active ingredient can be varied as occasion demands. However, generally 0.5~20% by weight is suitable in dust or granular preparations and 5~80% by weight is suitable in emulsion or water-dispersible preparations.

The application amount of the agricultural-horticultural fungicide of the present invention is varied depending upon species of the used compound, kind of disease, condition and degree of affection, environmental conditions, type of the used preparation, etc. In the case of dust or granular preparations, which are applied as they are, the concentration of the active ingredient may well be selected in the range of 10~500 g per 10 ares. In the case of an emulsion or a water-dispersed preparation, which is used in the form of liquid, the concentration is selected in the range of 10~2000 ppm.

The compounds of the present invention exhibit a remarkable effect for Alternaria sooty spot of Chinese mustard (*Brassica rapa var. pervidis*) caused by *Alternaria brassicicola*, Alternaria leaf spot of apple, black spot disease of pear, cucumber gray mold, cucumber downy mildew, rice blast, late bright of tomato and potato, gray mold of egg plant and grape, etc., as well as disease injury disseminated through soil or seeds. The effect is exhibited both preventive and curative, and is durable. Further, the compounds of the present invention are highly non-toxic to homoiothermic animals and aquatic animals.

SPECIFIC DESCRIPTION OF THE INVENTION

Now the invention will be described specifically with respect to preparation of the compounds and formulation of agricultural-horticultural fungicidal compositions by way of working examples. In these examples percentages referred to are all by weight.

PREPARATION EXAMPLE 1

Synthesis of
2-(4-chlorobenzylsulfonyl)-7-methyl-5H-1,3,4-thiadiazolo[3,2-a]pyrimidin-5-one (Compound 2)

In 500 ml of chloroform, 16.4 g of 2-(4-chlorobenzylthio)-7-methyl-5H-1,3,4-thiadiazolo[3,2-a]pyrimidin-5-one and 26.2 g of m-chloroperbenzoic acid were dissolved and the mixture was stirred for 10 hours at −10~5° C. An aqueous solution of sodium hydrogen carbonate was added to the mixture to quench the reaction. Chloroform was added for extraction, the organic layer was washed with water and dried over anhydrous sodium sulfate. The solvent was distilled off, the residue was purified by column chromatography on a silica gel with an ethyl acetate:toluene (1:9) mixture as an eluent. The solvent was distilled off and 9.5 g of 2-(4-chlorobenzylsulfonyl)-7-methyl-5H-1,3,4-thiadiazolo[3,2-a]pyrimidin-5-one was obtained.

m.p. 192°~194° C., yield 53%.

PREPARATION EXAMPLE 2

Synthesis of
2-benzenesulfonyl-6-methyl-5H-1,3,4-thiadiazolo[3,2-a]pyrimidin-5-one (Compound 40)

In 165 ml of methanol, 4.1 g of 2-phenylthio-6-methyl-5H-1,3,4-thiadiazolo[3,2-a]pyrimidin-5-one was dissolved. A dispersion of 40.3 g of OXONE ® suspended in 165 ml of water was added to the methanol solution, and the resulting mixture was warmed to 60° C. and stirred for 2 hours. After cooling, chloroform was added for extraction, the organic layer was washed with a sodium thiosulfate aqueous solution, a sodium hydrogen carbonate aqueous solution and water respectively. After the organic layer was dried over anhydrous sodium sulfate, the solvent was distilled off. The residue was recrystallized from a toluene/ethanol (1:1) mixture and thus 1.2 g of 2-benzenesulfonyl-6-methyl-5H-1,3,4-thiadiazolo[3,2-a]pyrimidin-5-one was obtained.

m.p. 198°~200° C. Yield 26%.

PREPARATION EXAMPLE 3

Synthesis of
7-fluoro-2-heptanesulfonyl-6-methyl-5H-1,3,4-thiadiazolo[3,2-a]pyrimidin-5-one (Compound 33)

In 270 ml of methanol, 4.7 g of 7-fluoro-2-heptylthio-6-methyl-5H-1,3,4-thiadiazolo[3,2-a]pyrimidin-5-one was dissolved. A dispersion of 77.8 g of OXONE ® in 270 ml of water was added to the methanol solution. The residue obtained by the same procedure as in Example 2 was purified by column chromatography on a silica gel with an ethylacetate/n-hexane (2:3) mixture as an eluent. The solvent was distilled off and the residue was recrystallized from ethanol, and thus 2.7 g of 7-fluoro-2-heptanesulfonyl-6-methyl-5H-1,3,4-thiadiazolo-[3,2-a]pyrimidin-5-one was obtained.

m.p. 143°~146° C.
Yield 57%.

PREPARATION EXAMPLE 4

Synthesis of
2-(4-chlorobenzylthio)-7-methyl-5H-1,3,4-thiadiazolo[3,2-a]pyrimidin-5-one (intermediate)

In 35 ml of water and 70 ml of ethanol, 12.8 g of 2-amino-5-mercapto-1,3,4-thiadiazol and 43 g of sodium hydroxide were added. To this mixture, 14.8 g of 4-chlorobenzyl chloride was added and the mixture was stirred at room temperature for 1 hour. Water was added and the reaction mixture was filtered. The residue was washed with water and an ethanol/n-hexane (1:1) mixture, and was dried under reduced pressure, and thus 23:1 g of 2-amino-5-(4-chlorobenzylthio)-1,3,4-thiadiazole was obtained.

m.p. 162°~164° C. Yield 93%.

Twenty point two (20.2) g of the thus obtained 2-amino-5-(4-chlorobenzylthio)-1,3,4-thiadiazole and 12.2 g of ethyl acetoacetate were mixed with 24 g of polyphosphoric acid and the mixture was stirred at 130°~150° C. for 45 minutes. After cooling, water was added to the mixture, the mixture was extracted with chloroform, and the organic layer was washed with a sodium hydrogen carbonate aqueous solution and water respectively. The organic layer was dried over anhydrous sodium sulfate, and the solvent was distilled off. The residue was recrystallized from ethanol and thus 21.3 g of 2-(4-chlorobenzylthio)-7-methyl-5H-1,3,4-thiadiazolo[3,2-a]pyrimidin-5-one was obtained.

m.p. 138.5°~139.5° C. Yield 84%.

PREPARATION EXAMPLE 5

Synthesis of
2-phenylthio-6-methyl-5H-1,3,4-thiadiazolo[3,2-a]pyrimidin-5-one (intermediate)

In a mixture of 20 ml of water and 30 ml of ethanol, 7.3 g of thiophenol and 4.5 g of potassium hydroxide were added. To this solution, 11.7 g of 2-amino-5-bromo-1,3,4-thiadiazole was added, and the mixture was heated to 82° C. and stirred for 2 hours. After cooling, water was added and the mixture was filtered. The residuewas washed with water and n-hexane respectively, dried under reduced pressure, and thus 10.8 g of 2-amino-5-phenylthio-1,3,4-thiadiazole was obtained.

m.p. 202°~203° C. Yield 77%.

Seven point two (7.2) g of the thus obtained 2-amino-5-phenylthio-1,3,4-thiadiazole and 4.9 g of ethyl 3-hydroxy-2-methyl-2-propenoate were mixed with 13 g of polyphosphoric acid. By the same procedure as in Preparation Example 4, 5.9 g of 2-phenylthio-6-methyl-5H-1,3,4-thiadiazolo[3,2-a]pyrimidin-5-one was obtained.

m.p. 141°~143° C. Yield 58%.

PREPARATION EXAMPLE 6

Synthesis of 7-fluoro-2-heptylthio-6-methyl-5H-1,3,4-thiadiazolo[3,2-a]pyrimidin-5-one (intermediate)

In 32 ml of water and 32 ml of ethanol, 27.2 g of 2-amino-5-mercapto-1,3,4-thiadiazole and 9.0 g of sodium hydroxide were added. To this solution, 45.2 g of 1-iodoheptane was added, and the mixture was stirred at 60° C. for 2 hours. After cooling, water was added to the mixture and the mixture was filtered. The residue was washed with water, dried under reduced pressure, and recrystallized from an ethanol/n-hexane (1:1) mixture. Thus 36.1 g of 2-amino-5-heptylthio-1,3,4-thiadiazole was obtained.

m.p. 112°~113° C. Yield 78%.

A mixture of 19.7 g of the thus obtained 2-amino-5-heptylthio-1,3,4-thiadiazole, 40.9 g of bis (2,4,6-trichlorophenyl) 2-methyl-malonate and 55 ml of chlorobenzene was stirred at 140°~144° C. for 45 minutes. After cooling, n-hexane was added thereto, the precipitate was collected by filtration. Further n-hexane was added to the filtrate, and the precipitate was collected. The collected precipitates were combined. The combinedprecipitate was washed with n-hexane and thus 21.2 g of 2-heptylthio-7-hydroxy-6-methyl-5H-1,3,4-thiadiazolo-[3,2-a]pyrimidin-5-one was obtained.

m.p. 141°~143° C.

Yield 78%.

A mixture of 19.5 g of the thus obtained 2-heptylthio-7-hydroxy-6-methyl-5H-1,3,4-thiadiazolo-[3,2-a]pyrimidin-5-one, 38 g of phosphorus oxychloride and 13.6 g of phosphorus pentachloride was warmed to 77°~88° C. and was stirred for 2 hours. The reaction solution was concentrated under reduced pressure, thereafter the residue was dissolved in toluene, and the solution was washed with a potassium carbonate aqueous solution and water respectively. After the solution was dried over anhydrous sodium sulfate, the solvent was distilled off and the residue was purified by column chromatography on a silica gel with an ethyl acetate/n-hexane (2:3) mixture as an eluent. After the solvent was distilled off, 19.0 g of 7-chloro-2-heptylthio-6-methyl-5H-1,3,4-thiadiazolo-[3,2-a]pyrimidin-5-one was obtained.

m.p. 79°~81° C.

Yield 92%.

A solution of 8.6 g of the thus obtained 7-chloro-2-heptylthio-6-methyl-5H-1,3,4-thiadiazolo[3,2-a]pyrimidin-5-one, 3.0 g of spray dry potassium fluoride and 32 ml of sulfolane was heated at 205°~225° C. in a stream of nitrogen for 1 and half hours. After cooling, water was added to the mixture, and the mixture was extracted with toluene. The toluene layer was collected and washed with water. The toluene phase was dried over anhydrous sodium sulfate, the solvent was distilled off. The residue was purified by column chromatography on a silica gel with an ethyl acetate/n-hexane (1:3) mixture as an eluent. After the solvent was distilled off, 5.2 g of 7-fluoro-2-heptylthio-6-methyl-5H-1,3,4-thiadiazolo[3,2-a]pyrimidin-5-one was obtained.

m.p. 78°18 91° C. Yield 63%.

PREPARATION EXAMPLE 7

Synthesis of 2-hexanesulfonyl-7-(1-propynyl)-5H-1,3,4-thiadiazolo[3,2-a]pyrimidin-5-one (Compound 115)

In 225 ml of methanol, 6.6 g of 2-hexylthio-7-(1-propynyl)-5H-1,3,4-thiadiazolo[3,2-a]pyrimidin-5-one was dissolved. A dispersion of 51.2 g of OXONE ® suspended in 180 ml of water was added to the methanol solution, and the resulting mixture was warmed to 60°~65° C. and stirred for 50 minutes. After cooling, the mixture was extracted with chloroform, and the organic layer was washed with a sodium thiosulfate aqueous solution and water respectively, and dried over anhydrous sodium sulfate. The solvent was distilled off and the residue was purified by silica gel column chromatography using an ethyl acetate/toluene mixture as an eluent, and was recrystallized from ethanol. Thus 2.6 g of 2-hexanesulfonyl-7-(1-propynyl)-5H-1,3,4-thiadiazolo[3,2-a]pyrimidin-5-one was obtained.

m.p. 122°~125° C. Yield 41%.

PREPARATION EXAMPLE 8

Synthesis of 6-chloro-7-fluoro-2-hexanesulfonyl-5H-1,3,4-thiadiazolo[3,2-a]pyrimidin-5-one (Compound 121)

In 20 ml of acetic acid, 2.8 g of 6-chloro-7-fluoro-2-hexylthio-5H-1,3,4-thiadiazolo[3,2-a]pyrimidin-5-one and 0.14 g of sodium tungstate dihydrate were dissolved. To this acetic acid solution, 8.9 g of a 20% hydrogen peroxide solution was added dropwise over a 20 minute period. The solution was warmed to 60°~65° C. and stirred for 45 minutes. After cooling, the solution was diluted with water and extracted with chloroform. The organic layer was washed with water once, and was treated in the same manner as in Preparation Example 7. The thus obtained residue was recrystallized from ethanol and 2.0 g of 6-chloro-7-fluoro-2-hexanesulfonyl-5H-1,3,4-thiadiazolo[3,2-a]pyrimidin-5-one was obtained.

m.p. 185°~188° C. Yield 65%.

PREPARATION EXAMPLE 9

Synthesis of 2-heptanesulfonyl-6-methoxy-5H-1,3,4-thiadiazolo[3,2-a]pyrimidin-5-one (Compound 94)

In 55 ml of methanol, 3.3 g of 2-heptylthio-6-methoxy-5H-1,3,4-thiadiazolo[3,2-a]pyrimidin-5-one was dissolved. A dispersion of 19.4 g of OXONE ® suspended in 70 ml of water was added to the methanol solution, and the resulting mixture was warmed to 65° C. and stirred for 1 hour. The residue obtained by the same procedure as in Preparation Example 7 was recrystallized from ethanol and thus 1.8 g of 2-heptanesulfonyl-6-methoxy-5H-1,3,4-thiadiazolo[3,2-a]pyrimidin-5-one was obtained.

m.p. 106°~109° C. Yield 51%.

PREPARATION EXAMPLE 10

Synthesis of 6-ethynyl-2-heptanesulfonyl-5H-1,3,4-thiadiazolo[3,2-a]pyrimidin-5-one (Compound 87)

In 180 ml of methanol, 2.8 g of 6-ethynyl-2-heptylthio-5H-1,3,4-thiadiazolo[3,2-a]pyrimidin-5-one was dissolved. A dispersion of 20 g of OXONE ® in 66 ml of water was added to the methanol solution and the resulting mixture was stirred for 24 hours at room temperature. The residue obtained by the same procedure as in Preparation Example 7 was separated by silica gel column chromatography using an ethyl acetate/toluene mixture as an eluent and was recrystallized from an ethanol/chloroform mixture, and thus 1.3 g of 6-ethynyl-2-heptanesulfonyl-5H-1,3,4-thiadiazolo[3,2-a]pyrimidin-5-one was obtained.

m.p. 180°~182° C. Yield 39%.

PREPARATION EXAMPLE 11

Synthesis of 2-hexylthio-7-(1-propynyl)-5H-1,3,4-thiadiazolo[3,2-a]pyrimidin-5-one (intermediate)

In 190 ml of ethanol and 240 ml of water, 81.5 g of 2-amino-5-mercapto-1,3,4-thiadiazole and 26.9 g of sodium hydroxide were added. To this solution, 99 g of 1-bromohexane was added and the resulting mixture was warmed to 60°~70° C. and stirred for 2 hours. After cooling, water was added to the reaction mixture, and the resulting solution was filtered. The residue was washed with water and dried under reduced pressure. The dried residue was recrystallized from an ethanol/hexane mixture, and thus 100.5 g of 2-amino-5-hexylthio-1,3,4-thiadiazole was obtained.

m.p. 113°~115° C. Yield 77%.

A mixture of 65.2 g of the thus obtained 2-amino-5-hexylthio-1,3,4-thiadiazole, 141.7 g of bis(2,4,6-trichlorophenyl) malonate and 240 ml of chlorobenzene was heated to 137°~140° C. and stirred for 1 hour. After cooling, hexane was added to the mixture, and the formed precipitate was separated by filtration, the residue was washed with hexane, and thus 74.7 g of 2-hexylthio-7-hydroxy-5H-1,3,4-thiadiazolo[3,2-a]pyrimidin-5-one was obtained.

m.p. 187°~192° C.
Yield 87%.

A mixture of 23.5 g of the thus obtained 2-hexylthio-7-hydroxy-5H-1,3,4-thiadiazolo[3,2-a]pyrimidin-5one, 17.8 g of phosphorus pentachloride and 50.4 g of phosphorus oxychloride was heated to 65°~90° C. and was stirred for 2 hours. The reaction mixture was concentrated under reduced pressure. The residue was dissolved in toluene. The solution was washed with a potassium carbonate aqueous solution and water respectively, and dried over anhydrous sodium sulfate. The solvent was distilled off, and the residue was separated by silica gel column chromatography using an ethyl acetate/toluene mixture as an eluent and 10.2 g of 7-chloro-2-hexylthio-5H-1,3,4-thiadiazolo[3,2-a]pyrimidin-5-one was obtained.

m.p. 95°~96° C.
Yield 41%.

A solution of 8.4 g of the thus obtained 7-chloro-2-hexylthio-5H-1,3,4-thiadiazolo[3,2-a]pyrimidin-5-one and 88.2 g of a 57% hydroiodic acid aqueous solution was heated to 95°~110° C. and stirred for 2 hours. After cooling, the solution was filtered. The residue was washed with water and dissolved in toluene. The toluene solution was washed with a sodium hydrogen carbonate aqueous solution, a sodium thiosulfate aqueous solution and water respectively and dried over anhydrous sodium sulfate. The solvent was distilled off and thus 9.8 g of 80% pure 7-iodo-2-hexylthio-5H-1,3,4-thiadiazolo[3,2-a]pyrimidin-5-one was obtained.

Yield 72%.

Into a solution of 8.6 g of the thus obtained 7-iodo-2-hexylthio-5H-1,3,4-thiadiazolo[3,2-a]pyrimidin-5one, 11 g of triethylamine, 0.15 g of bis(triphenylphosphine)palladium(II) chloride, 0.04 g of cuprous iodide and 33 ml of tetrahydrofurane, 2.6 g of 1-propyne was introduced through a bubbling glass tube under ice-cold-water chilling and constant stirring over a 1 hour period. Thereafter, the solution was further stirred at room temperature for 30 minutes, and 0.23 g of bis(triphenylphosphine)palladium(II) chloride and 0.06 g of cuprous iodide were added. The solution was stirred further for 4 hours. Then toluene was added, and the solution was filtered, and the filtrate was concentrated under reduced pressure. The residue was dissolved in toluene, the solution was washed with water and dried over anhydrous sodium sulfate. The solvent was distilled off and the residue was recrystallized from an ethanol/hexane mixture and thus 3.9 g of 7-(1-propynyl)-2-hexylthio-5H-1,3,4-thiadiazolo[3,2-a]pyrimidin-5-one was obtained.

m.p. 94°~97° C.
Yield 72%.

PREPARATION EXAMPLE 12

Synthesis of 6-chloro-7-fluoro-2-hexylthio-5H-1,3,4-thiadiazolo[3,2-a]pyrimidin-5-one (intermediate)

A mixture of 30 g of 2-hexylthio-7-hydroxy-5H-1,3,4-thiadiazolo[3,2-a]pyrimidin-5-one, 21.3 g of sulfuryl chloride, 0.85 g of ferric chloride and 113 g of phosphorus oxychloride was heated to 110° C. and stirred for 1.5 hours. After cooling, the reaction solution was concentrated under reduced pressure. To the residue, toluene and water were added, and extraction was carried out. The organic layer was washed with water, a sodium hydrogen carbonate aqueous solution and water respectively, and dried over anhydrous sodium sulfate. The solvent was distilled off and the residue was purified by silica gel column chromatography using an ethyl acetate/toluene mixture as an eluent. Thus 18.8 g of 6,7-dichloro-2-hexylthio-5H-1,3,4-thiadiazolo[3,2-a]pyrimidin-5-one was obtained.

Yield 75%.

A solution of 4.4 g of the thus obtained 6,7-dichloro-2-hexylthio-5H-1,3,4-thiadiazolo[3,2-a]pyrimidin-5-one, 2.2 g of spray dry potassium fluoride and 20 ml of sulfolane was heated to 185°~200° C. and stirred for 45 minutes. After cooling, toluene and water were added to the reaction solution and extraction was carried out. The organic layer was washed with water and dried over anhydrous sodium sulfate. The solvent was distilled off and the residue was separated by silica gel column chromatography using an ethyl acetate/toluene mixture as an elutant. Thus 3.0 g of 6-chloro-7-fluoro-2-hexylthio-5H-1,3,4-thiadiazolo[3,2-a]pyrimidin-5-one was obtained.

m.p. 105°~111° C.
Yield 71%.

PREPARATION EXAMPLE 13

Synthesis of 2-heptylthio-6-methoxy-5H-1,3,4-thiadiazolo[3,2-a]pyrimidin-5-one (intermediate)

In 185 ml of ethanol and 185 ml of water, 68.0 g of 2-amino-5-mercapto-1,3,4-thiadiazole and 22.4 g of sodium hydroxide were added. To this mixture, 84.6 g of 1-bromoheptane was added, and the resulting mixture was warmed to 60° C. and stirred for 2 hours. After cooling, water was added and the mixture was filtered. The residue was washed with water, dried under reduced pressure, and recrystallized from an ethanol/hexane mixture. Thus 90.2 g of 2-amino-5-heptylthio-1,3,4-thiadiazole was obtained.

m.p. 112°~113° C.
Yield 78%.

A mixture of 4.7 g of 2-amino-5-heptylthio-1,3,4-thiadiazole, 3.3 g of propyl 3-hydroxy-2-methoxy-2-methoxy-2-propenoate and 12 g of polyphosphoric acid was heated to 130°~135° C. and stirred for 30 minutes. After cooling, water and chloroform were added to the mixture and extraction was carried out. The organic layer was washed with a sodium hydrogen carbonate aqueous solution and water respectively, and dried over anhydrous sodium sulfate. The solvent was distilled off, and the residue was separated by silica gel column chromatography using an ethyl acetate/toluene mixture as an eluent. Thus 4.0 g of 2-heptylthio-6-methoxy-5H-1,3,4-thiadiazolo[3,2-a]pyrimidin-5-one was obtained.

m.p. 68°~71° C.
Yield 64%.

PREPARATION EXAMPLE 14

Synthesis of 6-ethynyl-2-heptylthio-5H-1,3,4-thiadiazolo[3,2-a]pyrimidin-5-one (intermediate)

A mixture of 20.1 g of 2-amino-5-heptylthio-1,3,4-thiadiazole, 20.0 g of ethyl 3-ethoxypropenoate and 23 g of polyphosphoric acid was heated to 130°~140° C. and stirred for 30 minutes. The residue obtained by the same procedure as in Preparation Example 13 was purified by silica gel column chromatography using an ethyl acetate/toluene mixture as an eluent. Thus 12.6 g of 2-heptylthio-5H-1,3,4-thiadiazolo[3,2-a]pyrimidin-5-one was obtained.

Yield 51%.

In 65 ml of acetic acid, 12.5 g of the thus obtained 2-heptylthio-5H-1,3,4-thiadiazolo[3,2-a]pyrimidin-5-one was dissolved. To this solution, 10.5 g of zinc chloride was added, and a solution of 10.5 g of iodine monochloride in 20 ml of acetic acid was added dropwise to the solution. Thereafter, the solution was warmed to 70°~80° C. and stirred for 1.5 hours. After cooling, chloroform and water were added and extraction was carried out. The organic layer was washed with a sodium hydrogen The organic layer was washed with a sodium hydrogen carbonate aqueous solution, a sodium thiosulfate aqueous solution and water respectively, and dried over anhydrous sodium sulfate. The solvent was distilled off and the residue was purified by silica gel column chromatography using an ethyl acetate/toluene mixture as an eluent. Thus 9.4 g of 2-heptylthio-6-iodo-5H-1,3,4-thiadiazolo[3,2-a]pyrimidin-5-one.

Yield 52%.

In a mixture of 50 ml of triethylamine and 100 ml of tetrahydrofurane, 8.0 g of the thus obtained 2-heptylthio-6-iodo-5H-1,3,4-thiadiazolo[3,2-a]pyrimidin-5-one was dissolved. To this solution, 0.68 g of bis(triphenylphosphine)palladium(II) chloride and 0.2 g of cuprous iodide were added as catalysts. To this mixture, a solution of 3.9 g of ethynyltrimethylsilane in 20 ml of triethylamine was added dropwise. The mixture was warmed to 60°~80° C. and stirred for 1 hour. Thereafter, further the same amounts as above of the catalysts and ethynyltrimethylsilane were added, and the mixture was stirred at 60°~70° C. for 3 hours. After cooling, the reaction mixture was filtered, and the filtrate was concentrated under reduced pressure. The residue was purified by silica gel column chromatography using an ethyl acetate/toluene mixture as an eluent, and 5.9 g of 2-heptylthio-6-trimethylsilylethynyl-5H-1,3,4-thiadiazolo[3,2-a]pyrimidin-5-one was obtained.

Yield 80%.

In 100 ml of tetrahydrofurane, 5.4 g of the thus obtained 2-heptylthio-6-trimethylsilylethynyl-5H-1,3,4-thiadiazolo[3,2-a]pyrimidin-5-one, and the solution was cooled to −65° C. in an acetone-dry ice bath. To the cooled solution, a solution of 0.93 g of tetrabutylammonium fluoride in 200 ml of tetrahydrofurane was added dropwise. The solution was stirred at −70~−65° C. for 1 hour. After the solution was brought to room temperature, the solution was filtered, and the filtrate was concentrated under reduced pressure. The residue was purified by silica gel column chromatography using an ethyl acetate/toluene mixture as an eluent and thus 3.0 g of 6-ethynyl-2-heptylthio-5H-1,3,4-thiadiazolo[3,2-a]pyrimidin-5-one was obtained.

m.p. 140°~142° C.
Yield 70%.

PREPARATION EXAMPLE 15

Synthesis of 2-hexanesulfonyl-7-methoxy-6-nitro-5H-1,3,4-thiadiazolo[3,2-a]pyrimidin-5-one In 50 ml of acetic acid, 1.9 g of 2-hexylthio-7-methoxy-6-nitro-5H-1,3,4-thiadiazolo[3,2-a]pyrimidin-5-one and 0.1 g of sodium tungstate dihydrate were dissolved. The solution was warmed to 50° C., and 3.1 g of a 30% hydrogen peroxide solution was added dropwise, and thereafter the solution was stirred at 52° C. for 1 hour. The reaction mixture was poured into 500 ml of water, and the formed precipitate was collected by filtration. The precipitate was washed with a sodium hydrogen sulfite aqueous solution and water, and recrystallized from ethanol. Thus 1.5 g of 2-hexanesulfonyl-7-methoxy-6-nitro-5H-1,3,4-thiadiazolo[3,2-a]pyrimidin-5-one as colorless prismatic crystals was obtained.

m.p. 150°~152° C.
Yield 71%.

PREPARATION EXAMPLE 16

Synthesis of 6-acetyl-2-hexanesulfonyl-5H-1,3,4-thiadiazolo[3,2-a]pyrimidin-5-one In 30 ml of acetic acid, 1.8 g of 6-acetyl-2-hexylthio-5H-1,3,4-thiadiazolo[3,2-a]pyrimidin-5-one was dissolved. To this solution, 2.0 g of a 30% hydrogen peroxide solution and 0.1 g of sodium tungstate dihydrate were added, and the solution was stirred at 55°-60° C. for 2 hours. The reaction mixture was extracted with chloroform, and the organic layer was washed with water, a sodium thiosulfate aqueous solution and water in this order, and dried over anhydrous sodium sulfate. The solvent was distilled off and the residue was recrystallized from an ethanol/benzene mixture. Thus 1.0 g of 6-acetyl-2-hexanesulfonyl-5H-1,3,4-thiadiazolo[3,2-a]pyrimidin-5-one was obtained.

m.p. 124°~125° C.
Yield 50%.

PREPARATION EXAMPLE 17

Synthesis of 6-cyano-2-heptanesulfonyl-5H-1,3,4-thiadiazolo[3,2-a]pyrimidin-5-one In 50 ml of acetic acid, 2.1 g of 6-cyano-2-heptylthio-5H-1,3,4-thiadiazolo[3,2-a]pyrimidin-5-one and 0.1 g of sodium tungstate dihydrate were dissolved. To this solution, 2.3 g of a 30% hydrogen peroxide solution was added dropwise so that the temperature of the solution did not exceed 50° C. Thereafter, the solution was stirred at 50° C. for 3 hours.

After the reaction was finished, water was added to the reaction mixture, and the deposited crystals were collected by filtration. This crude crystals were recrystallized from ethanol and 2 g of 6-cyano-2-heptylthio-5H-1,3,4-thiadiazolo[3,2-a]pyrimidin-5-one.

m.p. 130°~132° C.
Yield 85%.

PREPARATION EXAMPLE 18

Synthesis of 7-cyano-2-hexanesulfonyl-5H-1,3,4-thiadiazolo[3,2-a]pyrimidin-5-one In 40 ml of acetic acid, 2.2 g of 7-cyano-2-hexylthio-5H-1,3,4-thiadiazolo]3,2-a]pyrimidin-5-one was dissolved, 0.12 g of sodium tungstate dihydrate was added to the solution, and the solution was warmed to 45° C. and stirred. To this solution, 4.3 g of a 30% hydrogen peroxide mixed with 20 ml of acetic acid was added dropwise. Thereafter, the solution was stirred at 45°~50° C. for 2 hours. After cooled to room temperature, the solution was extracted with chloroform and water. The organic layer was washed with a sodium thiosulfate aqueous solution and water respectively. After dried over anhydrous sodium sulfate, the solvent was distilled off. The residue was recrystallized from ethanol, and thus 1.6 g of 7-cyano-2-hexanesulfonyl-5H-1,3,4-thiadiazolo[3,2-a]pyrimidin-5-one was obtained.

m.p. 144°-146° C.
Yield 65%.

PREPARATION EXAMPLE 19

Synthesis of 2-hexylthio-7-methoxy-6-nitro-5H-1,3,4-thiadiazolo[3,2-a)]pyrimidin-5-one (intermediate)

Seventy-six (76) grams of 2-amino-5-hexylthio-1,3,4-thiadiazole and 170 g of bis(2,4,6-trichlorophenyl) malonate were mixed with 200 ml of chlorobenzene, the mixture was stirred under refluxing for 1 hour. After the reaction was finished, the reaction mixture was cooled, and the formed precipitate was collected by filtration and washed with ether. Thus 82 g of white powder of 2-hexylthio-7-hydroxy-5H-1,3,4-thiadiazolo[3,2-a]pyrimidin-5-one was obtained.

m.p. 193°~197° C.
Yield 82%.

In 800 ml of acetic acid, 78 g of 2-hexylthio-7-hydroxy-5H-1,3,4-thiadiazolo[3,2-a]pyrimidin-5-one was suspended. To this suspension, 120 ml of fuming nitric acid was added dropwise at room temperature. After stirred for 3 hours the reaction mixture was cooled, and the formed precipitate was collected by filtration and washed with ether. Thus 84.5 g of colorless filament-like crystals of 2-hexylthio-7-hydroxy-6-nitro-5H-1,3,4-thiadiazolo-[3,2-a]pyrimidin-5-one.

m.p. 139°~141° C.
Yield 94%.

In 240 ml of phosphorus oxychloride, 66 g of 2-hexylthio-7-hydroxy-6-nitro-5H-1,3,4-thiadiazolo-[3,2-a]pyrimidin-5-one was suspended, and 24 g of N,N-dimethylaniline was added dropwise to the suspension at room temperature. The mixture was stirred for 2 hours under refluxing. The phosphorus oxychloride in the reaction mixture was distilled off under reduced pressure at 50° C. The residue was poured into 1 l of ice water, and deposited crystals were collected by filtration. The crystals were recrystallized from ethanol, and thus 58.4 g of pale yellow scaly crystals of 7-chloro-2-hexylthio-6-nitro-5H-1,3,4-thiadiazolo[3,2-a]pyrimidin-5-one was obtained.

m.p. 84.5°~86° C.
Yield 83%.

To 50 ml of methanol, 3.0 g of 7-chloro-2-hexylthio-6-nitro-5H-1,3,4-thiadiazolo[3,2-a]pyrimidin-5-one and 1.0 g of pyridine were added, and the mixture was stirred under refluxing for 30 minutes. Water was added to the reaction mixture and the organic layer was extracted with ethyl acetate. The ethyl acetate solution was dried over anhydrous magnesium sulfate, and the solvent was distilled off. The residue was purified by silica gel column chromatography using an ethyl acetate/hexane mixture as an eluent. Thus 1.9 g of brown transparent viscous liquid of 2-hexylthio-7-methoxy-6-nitro-5H-1,3,4-thiadiazolo[3,2-a]pyrimidin-5-one was obtained.

Yield 63%.

PREPARATION EXAMPLE 20

Synthesis of 6-acetyl-2-heptylthio-5H-1,3,4-thiadiazolo[3,2-a]pyrimidin-5-one (intermediate)

In 60 ml of ethanol, 4.4 g of 2-amino-5-hexylthio-1,3,4-thiadiazole, and 2.4 g of N,N-dimethylformamidodimethylacetal were dissolved, and the solution was refluxed for 2 hours. After the reaction mixture was cooled to room temperature, the formed crystals were collected by filtration, washed with ethanol and dried. Thus 4.4 g of N'-2-(5-hexylthio-1,3,4-thiadiazolyl)-N,N-dimethylformamidin was obtained.

m.p. 89°~91° C.
Yield 81%.

Then a mixture of 70 ml of dried benzene, 4.4 g of N'-2-(5-hexylthio-1,3,4-thiadiazolyl)-N,N-dimethylformamidin and 2.7 g of diketene was refluxed for 6 hours. The reaction mixture was concentrated and the residue was purified by a silica gel column chromatography using an ethyl acetate/n-hexane (1:3) mixture as an elutant. The eluent was distilled off, and thus 1.8 g of 6-acetyl-2-hexylthio-5H-1,3,4-thiadiazolo[3,2-a]pyrimidin-5-one was obtained.

Yield 36%.

PREPARATION EXAMPLE 21

Synthesis of 6-cyano-2-heptylthio-5H-1,3,4-thiadiazolo[3,2-a]pyrimidin-5-one (intermediate)

Eight (8) grams of 2-amino-5-heptylthio-1,3,4-thiadiazole, 5 g of ethyl 3-ethoxy-2-propenoate, 10 g of polyphosphoric acid and 10 ml of xylene were mixed, and the mixture was vigorously agitated at 125° C. for 30 minutes.

After the reaction was finished, the reaction mixture was extracted with water and toluene. The organic layer was washed with a sodium hydrogen carbonate aqueous solution and then with water. The solvent was distilled off and the residue was recrystallized from a n-hexane/ethanol mixture and thus 7.4 g of 2-heptylthio-5H-1,3,4-thiadiazolo[3,2-a]pyrimidin-5-one was obtained.

Yield 75%.

In 50 ml of acetic acid, 7.4 g of 2-heptylthio-5H-1,3,4-thiadiazolo[3,2-a]pyrimidin-5-one and 5.3 g of zinc chloride were dissolved. Six point three (6.3) grams of iodine monochloride was added to the solution, and the mixture was stirred at 70°-80° C. for 1 hour.

After the reaction was finished, water and a salt water was added, and the deposited crystals were collected by filtration. The collected crystals were washed with water and isopropyl ether, and thus 7.7 g of 2-heptylthio-6-iodo-5H-1,3,4-thiadiazolo[3,2-a]pyrimidin-5-one was obtained.

Yield 72%.

In 70 ml of dimethylformamide, 7.7 g of 2-heptylthio-6-iodo-5H-1,3,4-thiadiazolo[3,2-a]pyrimidin-5-one was dissolved, and 3.4 g of cuprous cyanide, 1.8 g of sodium cyanide were added to the solution. The mixture was stirred at 130° C. for 3 hours.

After the reaction was finished, the reaction mixture was poured into water. Toluene was added to the mixture and the mixture was stirred well. The insoluble materials were collected by filtration with a filtration aid. The organic layer was washed with water and dried over anhydrous magnesium sulfate. The solvent was distilled off, and the remaining crude crystals were recrystallized from ethanol. Thus 2.1 g of 2-heptylthio-6-cyano-5H-1,3,4-thiadiazolo[3,2-a]pyrimidin-5-one was obtained.

Yield 37%.

PREPARATION EXAMPLE 22

Synthesis of 2-hexylthio-7-cyano-5H-1,3,4-thiadiaxolo[3,2-a]pyrimidin-5-one (intermediate)

In 100 ml of dimethylformamide, 6 g of 2-hexylthio-7-iodo-5H-1,3,4-thiadiazolo[3,2-a]pyrimidin-5-one was dissolved. To this solution, 1.77 g of copper cyanide and 0.97 g of sodium cyanide were added and the solution was stirred at 100° C. for 1 hour. After the reaction mixture was cooled to room temperature, it was wxtracted with chloroform and water. The organic layer was washed with water and dried over anhydrous sodium sulfate. Florisil® was added to the organic layer and it was shaken. The solvent was distilled off, and 2.3 g of 7-cyano-2-hexylthio-5H-1,3,4-thiadiazolo[3,2-a]pyrimidin-5-one was obtained.

Yield 51%.

FORMULATION EXAMPLE 1

Dust preparation

Two (2)% of Compound 1, 5% of diatomaceous earth and 93% of clay were homogeneously mixed and ground to give a dust preparation.

FORMULATION EXAMPLE 2

Water-dispersible preparation

Fifty (50)% of Compound 2, 45% of diatomaceous earth, 2% of sodium dinaphthylmethanesulfonate and 3% of sodium lignosulfonate were homogeneously mixed and ground to give a water-dispersible preparation.

FORMULATION EXAMPLE 3

Emulsion preparation

Thirty (30)% of Compound 33, 20% of cyclohexanone, 11% of polyoxyethylenealkylaryl ether, 4% of calcium alkylbenzenesulfonate and 35% of methylnaphthalene were homogeneously mixed and emulsified.

FORMULATION EXAMPLE 4

Granular preparation

Five (5)% of Compound 40, 2% of sodium salt of lauryl alcohol sulfate ester, 5% of sodium lignosulfonate, 2% of carboxymethylcellulose and 86% of clay were homogeneously mixed and ground. To this mixture, 20% of water was added, and the mixture was made into granules of 14–32 mesh by means of an extrusion granulator. The granules were dried and finished as a granular preparation.

Now the fungicidal activity of the compounds of the present invention will be explained by way of test examples.

TEST 1

Protective Effect on Alternaria sooty spot of Chinese mustard (Brassica rapa var. pervidis)

Seeds of Chinese mustard were sown in 9 cm×9 cm plastic pots, 12 seeds each in a pot, and grown for 7 days in a greenhouse to the cotiledonous stage. Onto the grown seedlings a water-dispersible preparation prepared in accordance with the above Formulation Example 2, which was diluted with water to 50 ppm, was sprayed at a rate of 10 ml per pot. After the sprayed preparation was air-dried, the plants were inoculated with a suspension of spores of the pathogenic fungus of Alternaria sooty spot disease (*Alternaria brassicicola*) by spraying and the pots were kept in a moist chamber at 30° C. After 3 days, number of lesions was counted and average numbers per leaf were recorded. The control activity was calculated in accordance with the following definition. Control Activity (%)

Control Activity (%) =

$$\left(1 - \frac{\text{Average no. of lesions in treated sections}}{\text{Average no. of lesions in non-treated sections}}\right) \times 100$$

The results are shown in Table 2.

TABLE 2

| Compound Tested | Control Activity |
|---|---|
| 1 | 63.9 |
| 2 | 72.7 |
| 3 | 96.2 |

TABLE 2-continued

| Compound Tested | Control Activity |
| --- | --- |
| 5 | 72.1 |
| 6 | 97.5 |
| 7 | 77.8 |
| 8 | 86.1 |
| 10 | 69.6 |
| 13 | 72.7 |
| 14 | 100 |
| 16 | 77.2 |
| 18 | 97.2 |
| 19 | 82.3 |
| 22 | 85.4 |
| 23 | 72.7 |
| 24 | 92.4 |
| 25 | 100 |
| 26 | 99.4 |
| 27 | 76.6 |
| 31 | 69.2 |
| 34 | 89.3 |
| 35 | 75.3 |
| 37 | 96.2 |
| 38 | 63.2 |
| 40 | 93.7 |
| Captan* | 51.2 |
| Untreated | 0 |

TEST 2

Control of apple Alternaria leaf spot

Young twigs with 6–7 leaves detached from an apple tree (variety: Indo) were put in a glass cylinder. A water-dispersible preparation prepared in accordance with the above Formulation Example 2 was diluted to 1500 ppm with water and sprayed thereonto. After air-dried, the plants were inoculated with a suspension of spores of the pathogenic fungus of Alternaria leaf spot (*Alternaria mali*) by spraying, and were kept in a moist chamber at 28° C. After 4 days, the damage index was worked out in accordance with the following standard and the control activity was calculated.

Damage Index (%) =

$$\frac{(n_1 \times 1) + (n_2 \times 2) + (n_3 \times 3) + (n_4 \times 4) + (n_5 \times 5)}{5N} \times 100$$

- N is the total number of the examined leaves.
- $n_1$ is the number of the affected leaves on which area of lesions is less than 5%
- $n_2$ is the number of the affected leaves on which area of lesions is less than 5~10%
- $n_3$ is the number of the affected leaves on which area of lesions is less than 11~25%
- $n_4$ is the number of the affected leaves on which area of lesions is less than 26~50%
- $n_5$ is the number of the affected leaves on which area of lesions is more than 51%
- $n_0$ represents no affection Control Activity (%) =

$$\left(1 - \frac{\text{Damage index in treated sections}}{\text{Damage index in untreated sections}}\right) \times 100$$

The results are shown in Table 3.

TABLE 3

| Compound Tested | Control Activity |
| --- | --- |
| 1 | 96.0 |
| 2 | 100 |
| 10 | 97.2 |
| 13 | 94.3 |
| 14 | 82.9 |

TABLE 3-continued

| Compound Tested | Control Activity |
| --- | --- |
| 34 | 97.2 |
| 35 | 100 |
| untreated | 0 |

TEST 3

Prevention of cucumber gray mold

Seeds of cucumber (variety: Sagami-hanjiro) were sown in 9 cm × 9 cm square plastic pots, 12 seeds each in a pot, and grown in a greenhouse for 7 days. Onto the young seedlings, which have grown to the cotyledonous stage, a water-dispersible preparation prepared in accordance with the above Formulation Example 2, which was diluted to the active ingredient concentration of 500 ppm with water, was sprayed at a rate of 10 ml per pot. After the sprayed preparation was air-dried, the plants were inoculated with a homogenized hyphal suspension of liquid culture of cucumber gray mold fungus (*Botrytis cinearea*) by spraying, and the pots were kept in a moist chamber at 20°~23° C. After four days, conditions of the affection were checked with respect to all the pots.

| Index of Affection | |
| --- | --- |
| 0: No affection | |
| 1: Affected area is less than | 25% |
| 2: Affected area is | 26~50% |
| 3: Affected area is | 51~75% |
| 4: Affected area is | more than 75% |

The results are shown in Table 4.

TABLE 4

| Compound Tested | Index of Affection | Compound Tested | Index of Affection |
| --- | --- | --- | --- |
| 1 | 0 | 47 | 1 |
| 3 | 1 | 48 | 0 |
| 5 | 0 | 49 | 0 |
| 7 | 1 | 50 | 0 |
| 8 | 1 | 51 | 0 |
| 9 | 0 | 52 | 0 |
| 10 | 0 | 53 | 0 |
| 13 | 0 | 54 | 0 |
| 14 | 0 | 55 | 1 |
| 18 | 0 | 56 | 0 |
| 19 | 1 | 57 | 0 |
| 20 | 0 | 58 | 0 |
| 22 | 0 | 59 | 0 |
| 23 | 0 | 60 | 0 |
| 24 | 0 | 61 | 1 |
| 25 | 0 | 62 | 0 |
| 26 | 0 | 63 | 0 |
| 27 | 0 | 64 | 0 |
| 28 | 0 | 65 | 1 |
| 29 | 1 | 66 | 0.5 |
| 30 | 0 | 68 | 0 |
| 31 | 0 | 69 | 0 |
| 32 | 0 | 70 | 0 |
| 33 | 0 | 71 | 0 |
| 34 | 0 | 72 | 0 |
| 35 | 0 | 73 | 0 |
| 37 | 0 | 75 | 1 |
| 40 | 0 | 76 | 0 |
| 41 | 0 | 77 | 1 |
| 42 | 0 | 78 | 0 |
| 43 | 0 | 79 | 0 |
| 44 | 0 | 80 | 0 |
| 45 | 0 | 81 | 0 |
| 46 | 0 | 82 | 1 |
| 84 | 0 | 108 | 0 |
| 85 | 2 | 109 | 0 |

TABLE 4-continued

| Compound Tested | Index of Affection | Compound Tested | Index of Affection |
|---|---|---|---|
| 86 | 1 | 110 | 0 |
| 87 | 1 | 112 | 1 |
| 88 | 0 | 113 | 0 |
| 89 | 0 | 114 | 0 |
| 90 | 1 | 115 | 0 |
| 91 | 0 | 116 | 0 |
| 92 | 0 | 117 | 1 |
| 93 | 0 | 118 | 1 |
| 94 | 0 | 119 | 1 |
| 95 | 0 | 120 | 0 |
| 96 | 1 | 121 | 0 |
| 97 | 1 | 122 | 0 |
| 98 | 2 | 125 | 0 |
| 99 | 2 | 126 | 0 |
| 100 | 0 | 127 | 0 |
| 101 | 1 | 128 | 0 |
| 102 | 0 | 130 | 0 |
| 103 | 0 | 131 | 0 |
| 104 | 0 | 132 | 0 |
| 105 | 0 | 153 | 0 |
| 106 | 1 | 164 | 0 |
| 107 | 0 | | |

The other compounds were also effective on cucumber gray mold.

TEST 4

Protective effect on rice blast

Each 20 seeds of rice (variety: Aichiasahi) were sown in flowerpots 9 cm in diameter of white porcelain, and grown in a greenhouse for 3~4 weeks. Onto the young seedlings, at the 4 leaf stage, a water-dispersible preparation prepared in accordance with the above Formulation Example 2, which was diluted with water to the active ingredient concentration of 500 ppm was sprayed at a rate of 10 ml per pot. After the sprayed preparation was air-dried, the seedlings were inoculated spores of the pathogenic fungus of rice blast (*Pyricularia oryzae*) suspended in water by spraying in a moist chamber at 25° C. The disease development was allowed in the greenhouse for 5 days. The numbers of lesions were counted and the control activity was calculated.

Control Activity (%) =

$$\left(1 - \frac{\text{No. of lesions in treated sections}}{\text{No. of lesions in non-treated sections}}\right) \times 100$$

The results are shown in Table 5.

TABLE 5

| Compound Tested | Control Activity | Compound Tested | Control Activity |
|---|---|---|---|
| 42 | 79.3 | 78 | 79.7 |
| 43 | 84.4 | 79 | 90.3 |
| 44 | 86.0 | 80 | 88.2 |
| 45 | 93.3 | 81 | 89.0 |
| 46 | 92.1 | 82 | 75.4 |
| 47 | 79.1 | 83 | 100.0 |
| 48 | 98.0 | 84 | 64.4 |
| 49 | 97.2 | 85 | 86.8 |
| 50 | 89.4 | 86 | 91.3 |
| 51 | 70.7 | 87 | 79.3 |
| 52 | 98.3 | 88 | 81.3 |
| 53 | 63.4 | 89 | 71.8 |
| 54 | 75.9 | 90 | 78.1 |
| 55 | 93.4 | 91 | 88.5 |
| 57 | 83.0 | 92 | 75.4 |
| 58 | 89.7 | 93 | 74.1 |
| 59 | 93.9 | 94 | 96.3 |
| 60 | 92.1 | 95 | 88.7 |
| 61 | 75.3 | 97 | 92.5 |
| 62 | 95.3 | 98 | 88.1 |
| 63 | 76.5 | 99 | 77.7 |
| 64 | 66.0 | 100 | 80.4 |
| 65 | 80.4 | 101 | 75.9 |
| 66 | 87.0 | 102 | 81.2 |
| 67 | 83.3 | 103 | 78.6 |
| 68 | 96.3 | 104 | 89.8 |
| 70 | 85.0 | 105 | 94.6 |
| 71 | 91.3 | 106 | 91.7 |
| 72 | 90.5 | 107 | 96.7 |
| 73 | 85.5 | 108 | 65.8 |
| 75 | 81.0 | 109 | 77.8 |
| 76 | 85.4 | 110 | 84.8 |
| 77 | 92.4 | 111 | 79.1 |
| 113 | 69.4 | 132 | 99.2 |
| 114 | 83.7 | 133 | 66.3 |
| 115 | 96.3 | 134 | 67.8 |
| 116 | 85.6 | 135 | 83.2 |
| 117 | 81.4 | 136 | 89.3 |
| 118 | 100.0 | 153 | 96.2 |
| 119 | 94.6 | 162 | 79.3 |
| 120 | 69.9 | 163 | 85.5 |
| 121 | 86.9 | 164 | 97.4 |
| 122 | 86.4 | 167 | 94.3 |
| 125 | 74.7 | 168 | 82.3 |
| 126 | 86.3 | 169 | 97.2 |
| 127 | 73.3 | 170 | 86.2 |
| 128 | 68.7 | 171 | 79.4 |
| 129 | 71.2 | 172 | 96.9 |
| 130 | 93.6 | 173 | 77.8 |
| 131 | 93.6 | 175 | 98.5 |

The other compounds were also effective on rice blast.

TEST 5

Control of tomato late blight (Field test)

Tomato seedlings (variety: Ohgata-Fukuju) were transplanted on 20th August, 1986. Plants which had grown to have 12~13 leaves were used for the test.

Each 5 plants were designated 1 plot and 3 plots underwent the same treatment.

Application of the fungicide was carried out three times on 30th September, 7th and 14th October. The fungicide was sprayed at a rate of 2 liters per each 3 plots.

Disease severity was examined on 21st October with respect to the fourth to ninth leaves. The degree of damage and control activity were calculated in accordance with the following definitions.

| Rating Index | Proportion of affected area |
|---|---|
| 0 | 0 |
| 1 | less than ⅓ |
| 2 | ⅓ to ⅔ |
| 3 | more than ⅔ |

Degree of Damage = [{Σ (No. of leaves of Index 1) × 1 +

(No. of leaves of Index 2) × 2 +

(No. of leaves of Index 3) × 3}/

(Total no. of leaves) × 3] × 100

Control Activity =

$$\left(1 - \frac{\text{Degree of Damage in Treated Sections}}{\text{Degree of Damage in Untreated Sections}}\right) \times 100$$

Results are shown in Table 6.

TABLE 6

| Compound Tested | Conc. (ppm) | Degree of Damage (%) | Control Activity (%) |
|---|---|---|---|
| 91 | 500 | 3.2 | 96.7 |
| 94 | " | 8.3 | 91.5 |
| 103 | " | 4.8 | 95.1 |
| 104 | " | 0.8 | 99.2 |
| 113 | " | 6.5 | 93.4 |
| 115 | " | 1.2 | 98.8 |
| TPN* | 1000 | 26.2 | 73.3 |
| Untreated | | | 0 |

*TPN (tetrachloro-isophthalnitrile)

We claim:

1. A 5H-1,3,4-thiadiazolo[3,2-a]pyrimidin-5-one of the formula (I)

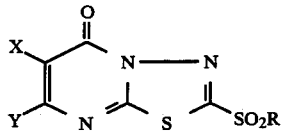

(I)

wherein X is hydrogen, Y is chlorine or fluorine, wherein when Y is chlorine, R is n-$C_4H_9$ or n-$C_6H_{13}$, and when Y is fluorine, R is n-$C_5H_{11}$ or n-$C_6H_{13}$.

2. The 5H-1,3,4-thiadiazolo[3,2-a]pyrimidin-5-one of claim 1, wherein Y is chlorine and R is n-$C_4H_9$.

3. The 5H-1,3,4-thiadiazolo[3,2-a]pyrimidin-5-one of claim 1, wherein Y is chlorine and R is n-$C_6H_{13}$.

4. The 5H-1,3,4-thiadiazolo[3,2-a]pyrimidin-5-one of claim 1, wherein Y is fluorine and R is n-$C_5H_{11}$.

5. The 5H-1,3,4-thiadiazolo[3,2-a]pyrimidin-5-one of claim 1, wherein Y is fluorine and R is n-$C_6H_{13}$.

6. An agricultural-horticultural fungicide composition comprising a 5H-1,3,4-thiadiazolo[3,2-a]pyrimidin-5-one of the formula (I)

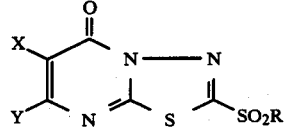

(I)

wherein X is hydrogen, Y is chlorine or fluorine, and wherein when Y is chlorine, R is n-$C_4H_9$ or n-$C_6H_{13}$, and when Y is fluorine, R is n-$C_5H_{11}$ or n-$C_6H_{13}$, and an agricultural-horticulturally acceptable carrier.

7. The agricultural-horticultural fungicide composition of claim 6, wherein Y is chlorine and R is n-$C_4H_9$.

8. The agricultural-horticultural fungicide composition of claim 6, wherein Y is chlorine and R is n-$C_6H_{13}$.

9. The agricultural-horticultural fungicide composition of claim 6, wherein Y is fluorine and R is n-$C_5H_{11}$.

10. The agricultural-horticultural fungicide composition of claim 6, wherein Y is fluorine and R is n-$C_6H_{13}$.

* * * * *